US012447248B2

(12) United States Patent
Rovatti et al.

(10) Patent No.: US 12,447,248 B2
(45) Date of Patent: Oct. 21, 2025

(54) APPARATUS FOR EXTRACORPOREAL TREATMENT OF BLOOD AND METHOD FOR DETERMINING A PARAMETER INDICATIVE OF THE PROGRESS OF AN EXTRACORPOREAL BLOOD TREATMENT

(71) Applicant: Gambro Lundia AB, Lund (SE)

(72) Inventors: Paolo Rovatti, Modena (IT); Marco Salsa, Modena (IT)

(73) Assignee: Gambro Lundia AB, Lund (SE)

( * ) Notice: Subject to any disclaimer, the term of this patent is extended or adjusted under 35 U.S.C. 154(b) by 593 days.

(21) Appl. No.: 17/429,271

(22) PCT Filed: Jan. 23, 2020

(86) PCT No.: PCT/EP2020/051684

§ 371 (c)(1),
(2) Date: Aug. 6, 2021

(87) PCT Pub. No.: WO2020/164881

PCT Pub. Date: Aug. 20, 2020

(65) Prior Publication Data

US 2022/0143284 A1 May 12, 2022

(30) Foreign Application Priority Data

Feb. 11, 2019 (EP) .................................... 19156537

(51) Int. Cl.

*A61M 1/16* (2006.01)
*A61M 1/34* (2006.01)
*G16H 20/40* (2018.01)

(52) U.S. Cl.

CPC ........ *A61M 1/1609* (2014.02); *A61M 1/1672* (2014.02); *A61M 1/341* (2014.02);
(Continued)

(58) Field of Classification Search

CPC .. A61M 1/1609; A61M 1/1672; A61M 1/341; A61M 1/3413; A61M 2205/3334;
(Continued)

(56) References Cited

U.S. PATENT DOCUMENTS 6,110,384 A 8/2000 Goux et al.
9,717,834 B2 8/2017 Wilt et al.
(Continued)

FOREIGN PATENT DOCUMENTS

CN 104321088 1/2015
EP 1108438 6/2001
(Continued)

OTHER PUBLICATIONS

Chinese Office Action—Application No. 202080013818.0 dated Dec. 26, 2023—18 pages.
(Continued)

*Primary Examiner* — Bradley R Spies
*Assistant Examiner* — Jeannie McDermott
(74) *Attorney, Agent, or Firm* — K&L Gates LLP

(57) ABSTRACT

An apparatus for extracorporeal treatment of blood (1) comprising a treatment unit, a blood withdrawal line, a blood return line, a preparation line and a spent dialysate line. A control unit (10) is configured to calculate values of a parameter relating to treatment effectiveness based on measures of the conductivity in the spent dialysate line. An upstream variation of the value of the characteristic ($Cd_{in}$) is caused in the fresh treatment liquid with respect to a prescription baseline ($Cd_{set}$) thereby causing a corresponding and timely delayed downstream variation of the same characteristic ($Cd_{out}$) in the spent liquid flowing in the spent dialysate line (13). An amplitude ($\Delta C_{in}$) and/or a duration over time ($\Delta T$) of the upstream variation are/is computed as a function of the flow rate (Qdial) of the fresh treatment
(Continued)

liquid in a preparation line (19) or of the parameter correlated to the flow rate (Qdial).

25 Claims, 11 Drawing Sheets

(52) U.S. Cl.
CPC .......... *A61M 1/3413* (2013.01); *G16H 20/40* (2018.01); *A61M 2205/3334* (2013.01)

(58) Field of Classification Search
CPC .............. A61M 1/1613; A61M 1/1607; A61M 1/1617; G16H 20/40
See application file for complete search history.

(56) References Cited

U.S. PATENT DOCUMENTS

| | | | | |
|---|---|---|---|---|
| 9,943,636 | B2 | 4/2018 | Fontanazzi et al. | |
| 2008/0015487 | A1* | 1/2008 | Szamosfalvi ....... | A61M 1/3413 210/323.1 |
| 2008/0097272 | A1 | 4/2008 | Daniel et al. | |
| 2015/0129499 | A1 | 5/2015 | Bene | |
| 2017/0326282 | A1 | 11/2017 | Wilt et al. | |
| 2018/0169315 | A1* | 6/2018 | Rovatti ............... | A61M 1/1609 |
| 2019/0134290 | A1* | 5/2019 | Pouchoulin ......... | A61M 1/1609 |

FOREIGN PATENT DOCUMENTS

| | | | | | |
|---|---|---|---|---|---|
| EP | 2687248 | A1 | | 1/2014 | |
| EP | 2732834 | | | 5/2014 | |
| EP | 2732834 | A1 | | 5/2014 | |
| FR | 2713936 | | | 6/1995 | |
| IT | TO960855 | | | 4/1998 | |
| WO | 2012161744 | | | 11/2012 | |
| WO | WO-2016188950 | A1 | * | 12/2016 | .......... A61M 1/1607 |
| WO | WO-2017186521 | A1 | * | 11/2017 | .......... A61M 1/1039 |

OTHER PUBLICATIONS

Chinese Search Report—Application No. 2020800138180 dated Jan. 23, 2020—3 pages.

* cited by examiner

APPARATUS FOR EXTRACORPOREAL TREATMENT OF BLOOD AND METHOD FOR DETERMINING A PARAMETER INDICATIVE OF THE PROGRESS OF AN EXTRACORPOREAL BLOOD TREATMENT

PRIORITY CLAIM

The present application is a National Phase of International Application No. PCT/EP2020/051684, filed Jan. 23, 2020, which claims priority to EP Application Serial No. 19156537.3, filed Feb. 11, 2019. The entire contents of each application are incorporated herein by reference and relied upon.

The invention relates to an apparatus for extracorporeal treatment of blood and a method for determining a parameter indicative of the progress of an extracorporeal blood treatment (referred to as effectiveness parameter), in particular a purification treatment whose purpose is to alleviate renal insufficiency, such as—without limitation—hemodialysis or hemodiafiltration. It is also disclosed a method of determining said parameter indicative of the progress of an extracorporeal blood treatment. For instance, the parameter may be one of:

- the concentration in the blood of a given solute (for example, sodium),
- the actual dialysance D or the actual clearance K of the exchanger for a given solute (the dialysance D and the clearance K representing the purification efficiency of the hemodialyzer or hemofilter used in the blood treatment),
- the dialysis dose administered after a treatment time t, which, according to the work of Sargent and Gotch, may be linked to the dimensionless ratio Kt/V, where K is the actual clearance in the case of urea, t the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp. 526-34). The dialysis dose—as above defined—is an integrated value $\int K(t)dt/V$ across a time interval, e.g. the dose after treatment time $t_n$ is the integral from the beginning of treatment until time instant $t_n$.

In an haemodialysis treatment a patient's blood and a treatment liquid approximately (but not necessarily) isotonic with blood flow are circulated in a respective compartment of haemodialyser, so that, impurities and undesired substances present in the blood (urea, creatinine, etc.) may migrate by diffusive transfer from the blood into the treatment liquid. The ion concentration of the treatment liquid is chosen so as to correct the ion concentration of the patient's blood. In a treatment by haemodiafiltration, a convective transfer by ultrafiltration, resulting from a positive pressure difference created between the blood side and the treatment-liquid side of the membrane of a haemodiafilter, is added to the diffusive transfer obtained by dialysis.

It is of interest to be able to determine, throughout a treatment session, one or more parameters indicative of the progress of the treatment so as to be able, where appropriate, to modify the treatment conditions that were initially fixed or to at least inform the patient and the medical personnel about the effectiveness of the treatment. The knowledge of one or more of the following parameters may make it possible to follow the progress of the treatment, and for instance may allow assessing the suitability of the initially fixed treatment conditions:

- concentration in the blood of a given solute (for example, sodium),
- actual dialysance D or the actual clearance K of the exchanger for solute (the dialysance D and the clearance K representing the purification efficiency of the exchanger),
- dialysis dose administered after a treatment time Kt/V, where K is the actual clearance in the case of urea, t the elapsed treatment time and V the volume of distribution of urea.

The determination of these parameters requires precise knowledge of a physical or chemical characteristic of the blood. As it can be understood, determination of this characteristic cannot in practice be obtained by direct measurement on a specimen for therapeutic, prophylactic and financial reasons. Indeed, it is out of the question taking—in the course of a treatment—multiple specimens necessary to monitor the effectiveness of the treatment from a patient who is often anemic; furthermore, given the risks associated with handling specimens of blood which may possibly be contaminated, the general tendency is to avoid such handling operations; finally, laboratory analysis of a specimen of blood is both expensive and relatively lengthy, this being incompatible with the desired objective of knowing the effectiveness of a treatment while the treatment is still ongoing.

Several methods have been proposed for in vivo determining haemodialysis parameters without having to take measurements on blood samples. Document EP 0547025 describes a method for determining the concentration of a substance, such as sodium, in a patient's blood subjected to a haemodialysis treatment. This method also makes it possible to determine the dialysance D—for example for sodium—of the haemodialyser used. The method comprises the steps of circulating a first and a second haemodialysis liquids having different sodium concentrations in succession through the haemodialyser, measuring the conductivity of the first and second dialysis liquids upstream and downstream of the haemodialyser, and computing the concentration of sodium in the patient's blood (or the dialysance D of the haemodialyser for sodium) from the values of the conductivity of the liquid which are measured in the first and second dialysis liquids upstream and downstream of the haemodialyser. Document EP 0658352 describes another method for the in vivo determination of haemodialysis parameters, which comprises the steps of: making at least a first and a second treatment liquids, having a characteristic (the conductivity, for example) associated with at least one of the parameters (the ion concentration of the blood, the dialysance D, the clearance K, Kt/V, for example) indicative of the treatment, flow in succession through the haemodialyser, the value of the characteristic in the first liquid upstream of the exchanger being different from the value of the characteristic in the second liquid upstream of the hemodialyzer; measuring, in each of the first and second treatment liquids, two values of the characteristic, respectively upstream and downstream of the hemodialyzer; making a third treatment liquid flow through the hemodialyzer while the characteristic of the second liquid has not reached a stable value downstream of the hemodialyzer, the value of the characteristic in the third liquid upstream of the hemodialyzer being different from the value of the characteristic in the second liquid upstream of the hemodialyzer; measuring two values of the characteristic in the third liquid, respectively upstream and downstream of the hemodialyzer; and computing at least one value of at least one parameter indicative of the progress of the treatment from the measured values of the characteristic in the first, second and third treatment liquids. Another method for the in vivo determination of the haemodialysis parameters which does not require taking measurements on blood samples is described in document EP 0920877. This method includes the steps of: making a treatment liquid flow through the exchanger, this treatment liquid having a characteristic which has an approximately constant nominal value upstream of the exchanger; varying the value of the characteristic upstream of the exchanger and then re-establishing the characteristic to its nominal value upstream of the exchanger; measuring and storing in memory a plurality of values adopted by the characteristic of the treatment liquid downstream of the exchanger in response to the variation in the value of this characteristic caused upstream of the exchanger; determining the area of a downstream perturbation region bounded by a baseline and a curve representative of the variation with respect to time of the characteristic; and computing the parameter indicative of the effectiveness of a treatment from the area of the downstream perturbation region and from the area of an upstream perturbation region bounded by a baseline and a curve representative of the variation with respect to time of the characteristic upstream of the exchanger. Document EP2732834 describes an apparatus for extracorporeal treatment of blood comprising a control unit which is configured to calculate values of a parameter relating to treatment effectiveness based on measures of the conductivity in the spent dialysate line. The value of the effectiveness parameter is calculated using one or more values representative of the conductivity in the spent dialysate line obtained relying on a mathematical model. The control unit causes an upstream (with respect to the treatment unit) variation of the value of a characteristic $Cd_{in}$ in the fresh treatment liquid with respect to a prescription baseline $Cd_{set}$ and then re-establishes the characteristic $Cd_{in}$ in the fresh treatment liquid to said prescription baseline $Cd_{set}$. The upstream variation causes a corresponding and timely delayed downstream (with respect to the treatment unit) variation of the same characteristic $Cd_{out}$ in the spent liquid flowing in the spent dialysate line. The control unit is configured to receive at least one parametric mathematical model, which puts into relation the characteristic $Cd_{in}$ in the fresh treatment liquid with the characteristic $Cd_{out}$ in the spent liquid. In order to determine the parameters of the parametric mathematical model, the control unit is configured to receive, e.g. from a sensor, measures of a plurality of values taken by a reference portion of the downstream variation of the characteristic $Cd_{out}$ in the spent liquid, wherein the reference portion, which is used by the control unit to characterize the mathematical model, has a duration $\Delta T_R$ significantly shorter than an entire duration $\Delta T_V$ of the downstream variation. The above described methods require a relatively short—compared to treatment time—modification of the value of a characteristic of the dialysis liquid (the conductivity, for example) and then the re-establishment of this characteristic to its initial value, which is generally the prescribed value. Since, deviations from the prescription are not desirable and since the above described methods require a minimum duration of the introduced modification, it derives that all these methods can be carried out only few times during a treatment. Document US 2001004523 describes a solution for continuously determining a parameter (D, Cbin, K, Kt/V) indicative of the effectiveness of an extracorporeal blood treatment comprising the steps of: causing a succession of sinusoidal variations in the characteristic (Cd) a treatment liquid upstream of the exchanger, continuously storing in memory a plurality of values ($Cd_{in1}$ . . . $Cd_{inj}$ . . . $Cd_{inp}$) of the characteristic (Cd) upstream of the exchanger, measuring and continuously storing in memory a plurality of values ($Cd_{out1}$ . . . $Cd_{outj}$ . . . $Cd_{outp}$) adopted by the characteristic (Cd) downstream of the exchanger in response to the variations in the characteristic (Cd) which are caused upstream of the exchanger, computing—each time that a predetermined number of new values ($Cd_{outj}$) of the characteristic (Cd) downstream of the exchanger has been stored—a parameter (D, Cbin, K, Kt/V) indicative of the effectiveness of the extracorporeal blood treatment, from a first series of values ($Cd_{inj}$) of the characteristic (Cd) upstream of the exchanger, from a second series of values ($Cd_{outj}$) of the characteristic (Cd) downstream of the exchanger. Another apparatus and method for determining a parameter indicative of the progress of an extracorporeal blood treatment is disclosed in document EP2687248, which describes an apparatus for extracorporeal treatment of blood wherein a control unit is configured to calculate values of a parameter relating to treatment effectiveness based on measures of the conductivity in the spent dialysate line subsequent to an alternating conductivity perturbation continuously imposed on the preparation line of fresh dialysis fluid. The control unit is configured to cause a plurality of consecutive and continuously repeated variations $V_k$ of the characteristic Cd around the prescription baseline $Cd_{set}$ in the liquid flowing in the preparation line. The variations define for instance a square wave around the prescription baseline. The above methods, which require a continuous perturbation in the characteristic of the treatment liquid, prevent execution of tasks, other than the one for measuring the effectiveness parameter, which may affect the concerned characteristic (conductivity/concentration) of the dialysis fluid. Indeed, while the control system is executing the effectiveness parameter detection, the control system will not execute other tasks taking an active control on the conductivity/composition of the dialysis liquid (e.g. tasks acting on the sodium concentration of the dialysis liquid in response to detection of certain parameters such as blood concentration). Furthermore, the system dynamic may depend on the working conditions, like dialysis fluid flow and dialyzer type and the system is not always able to converge to a meaningful solution. In some cases, with low dialysis fluid flows and filters with large areas (or vice versa) the measure could fail.

It is therefore an object of the present invention to provide an apparatus and a method configured to reliably calculate an effectiveness parameter one or more times during treatment without substantially impairing on prescription delivered to the patient and minimally affecting the operation flexibility of the blood treatment apparatus. In particular, it is an object to tune and optimize said method and an apparatus configured to calculate the effectiveness parameter even just one time without substantially impairing on prescription delivered to the patient. Additionally, it is an object providing a method and an apparatus which may be implemented with no need of high computational power and time machine. Another auxiliary object is an apparatus capable of operating in a safe manner A further auxiliary object is an apparatus capable of automatically calculate the effectiveness parameter and inform the operator accordingly.

SUMMARY

At least one of the above objects is substantially reached by an apparatus according to one or more of the appended claims. Apparatus and methods according to aspects of the invention and capable of achieving one or more of the above objects are here below described.

A 1st aspect concerns an apparatus for extracorporeal treatment of blood comprising:

a blood treatment unit having a primary chamber and a secondary chamber separated by a semi-permeable membrane;

a preparation line having one end connected to an inlet of a secondary chamber of the treatment unit and configured to convey fresh treatment liquid to the secondary chamber, the fresh treatment liquid presenting a characteristic which is one selected in the group of:

- conductivity in the fresh treatment liquid, and
- concentration of at least one substance in the fresh treatment liquid, a spent dialysate line having one end connected to an outlet of said secondary chamber and configured to remove spent liquid from the secondary chamber, the spent liquid presenting a characteristic which is one selected in the group of:

- conductivity in the spent liquid, and
- concentration of at least one substance in the spent liquid, a control unit configured for commanding execution of a task for determination of a parameter indicative of the effectiveness of the extracorporeal blood treatment, said task comprising the following steps:

- receiving at least one prescription baseline for the characteristic in the fresh treatment liquid;
- causing fresh treatment liquid to flow in the preparation line to the secondary chamber with the characteristic being at said prescription baseline;
- causing spent liquid to flow out of the secondary chamber into the spent dialysate line;
- causing an upstream variation of the value of the characteristic in the fresh treatment liquid with respect to said prescription baseline thereby causing a corresponding and timely delayed downstream variation of the same characteristic in the spent liquid flowing in the spent dialysate line; wherein the upstream variation has an amplitude (e.g., an absolute value variation of the characteristic) and a duration over time;
- computing at least one value of a parameter indicative of the effectiveness of the extracorporeal blood treatment by using values correlated to the upstream variation of the value of the characteristic in the fresh treatment liquid and values correlated to the downstream variation of the same characteristic in the spent liquid; optionally said values correlated to the upstream variation being set and/or measured and said values correlated to the downstream variation being measured and/or computed;

wherein said task further comprises:

- receiving a flow rate, or a parameter/parameters correlated to the flow rate, of the fresh treatment liquid in the preparation line;
- computing said amplitude and/or said duration over time of the upstream variation to be caused as a function of the flow rate or of the parameter correlated to the flow rate.

It is noted that having knowledge of the effluent flow rate and of the ultrafiltration flow rate is equivalent to knowing the flow rate of the fresh treatment liquid in the preparation line in a hemodialysis treatment; in an HDF treatment, knowledge of the effluent flow rate, infusion flow rate and of the ultrafiltration flow rate is equivalent to knowing the flow rate of the fresh treatment liquid in the preparation line.

It is also noted that the flow rate in the preparation line may be the set flow rate or a measured flow rate in the preparation line (if relevant, the same applies to the other mentioned flow rates, namely effluent flow rate, infusion flow rate, ultrafiltration flow rate).

In an additional aspect, the control unit execute the task including receiving a blood or plasma flow rate at the inlet of the primary chamber (e.g., set or measured blood/plasma flow rate) and including computing said amplitude and/or said duration over time of the upstream variation to be caused as a function of the blood or plasma flow rate, the computing of the amplitude and/or said duration over time of the upstream variation being made either as a function of both the flow rate (or of the parameter correlated to the flow rate) of the fresh treatment liquid in the preparation line and the blood (or plasma) flow rate, or as a function of the blood (or plasma) flow rate.

In an additional aspect, the control unit execute the task including receiving an efficiency parameter of the blood treatment unit, such as clearance or dialysance or mass transfer area coefficient $K_0A$, and including computing said amplitude and/or said duration over time of the upstream variation to be caused as a function of the efficiency parameter of the blood treatment unit, the computing of the amplitude and/or said duration over time of the upstream variation being made as a function of anyone of (let alone or in any combination) the flow rate (or of the parameter correlated to the flow rate) of the fresh treatment liquid in the preparation line, the blood (or plasma) flow rate and/or the efficiency parameter of the blood treatment unit. The efficiency parameter may be received from a memory or an input device of the apparatus, or may be calculated.

In a 2nd aspect according to the 1st aspect/previous aspects, the amplitude and/or the duration over time are/is higher if the flow rate of the fresh treatment liquid is lower and wherein the amplitude and/or the duration over time are/is lower if the flow rate of the fresh treatment liquid (and/or the blood or plasma flow rate) is higher.

In another aspect according to anyone of the previous aspects, the computed duration over time being between 50 s (being in particular a prefixed minimum duration over time) and 200 s (being in particular a prefixed maximum duration over time), optionally between 90 s and 150 s.

In another aspect according to anyone of the previous aspects, the characteristic is the conductivity in the fresh liquid and, optionally, the computed amplitude of conductivity being between 0.4 mS/cm (milliSiemens/centimeter) and 1.1 mS/cm, optionally between 0.5 mS/cm and 1 mS/cm (absolute values).

In another aspect according to anyone of the previous aspects, the flow rate of the fresh treatment liquid is lower than a prefixed maximum flow rate, being at most 850 ml/min, in particular the flow rate of the fresh treatment liquid being between 250 ml/min and 850 ml/min, optionally between 300 ml/min and 800 ml/min. The prefixed minimum flow rate of the fresh treatment liquid being for example 200 ml/min, or 300 ml/min.

In a 3rd aspect according to any one of the preceding aspects, the amplitude and/or the duration over time are/is inversely proportional with respect to the flow rate of the fresh treatment liquid (and/or the blood or plasma flow rate).

In a 4th aspect according to any one of the preceding aspects, computing the amplitude and/or the duration over time is performed through at least one mathematical formula; wherein optionally the mathematical formula is an interpolating curve; wherein optionally the interpolating curve is computed starting from “m” points, each point being defined by a flow rate value of the fresh treatment liquid and by a duration over time value and/or by an amplitude value corresponding to said flow rate value; wherein optionally "m" is equal to or greater than two.

In a 5th aspect according to any one of the preceding aspects, computing the amplitude and/or the duration over time is a function of a prefixed maximum flow rate of the fresh treatment liquid. The prefixed maximum flow rate of the fresh treatment liquid may be received from a memory or an input device of the apparatus, or may be calculated, based on e.g., an apparatus set-up.

In a further aspect according to any one of the preceding aspects, computing the amplitude and/or the duration over time is a function of a difference between the flow rate of the fresh treatment liquid and a prefixed maximum flow rate of the fresh treatment liquid. In particular, the difference between the flow rate of the fresh treatment liquid and a prefixed maximum flow rate of the fresh treatment liquid being multiplied by a multiplying factor.

In a further aspect according to any one of the preceding aspects, computing the amplitude and/or the duration over time is a function of a prefixed minimum flow rate of the fresh treatment liquid. The prefixed minimum flow rate of the fresh treatment liquid may be received from a memory or an input device of the apparatus, or may be calculated, based on e.g., an apparatus set-up.

In a further aspect according to any one of the preceding aspects, computing the amplitude and/or the duration over time is a function of a difference between a prefixed minimum flow rate of the fresh treatment liquid and the flow rate of the fresh treatment liquid. In particular, the prefixed minimum flow rate of the fresh treatment liquid and the flow rate of the fresh treatment liquid being multiplied by a multiplying factor.

In a further aspect according to any one of the preceding aspects, computing the amplitude and/or the duration over time is a function of a difference between a prefixed maximum flow rate of the fresh treatment liquid and a prefixed minimum flow rate of the fresh treatment liquid.

In a further aspect according to any one of the preceding aspects, computing the amplitude and/or the duration over time is a function of a prefixed maximum duration over time, in particular corresponding to a minimum flow rate of the apparatus. The prefixed maximum duration over time may be received from a memory or an input device of the apparatus, or may be calculated, based on e.g., an apparatus set-up.

In a further aspect according to any one of the preceding aspects, computing the amplitude and/or the duration over time is a function of a prefixed minimum duration over time, in particular corresponding to a maximum flow rate of the apparatus. The prefixed minimum duration over time may be received from a memory or an input device of the apparatus, or may be calculated, based on e.g., an apparatus set-up.

In a further aspect according to any one of the two preceding aspects, computing the amplitude and/or the duration over time is a function of a difference between the prefixed maximum duration over time and the prefixed minimum duration over time.

In a further aspect according to the preceding aspect, computing the amplitude and/or the duration over time is a function of a ratio between the difference between the prefixed maximum duration over time and the prefixed minimum duration over time and the difference between a prefixed maximum flow rate of the fresh treatment liquid and a prefixed minimum flow rate of the fresh treatment liquid. In particular, the ratio being the multiplying factor.

In a further aspect according to any one of the preceding aspects, computing the duration over time includes a sum of a main term based on the flow rate of the fresh treatment liquid and an auxiliary term being a time duration, in particular the time duration being a prefixed minimum duration over time or a prefixed maximum duration over time.

In a further aspect according to any one of the preceding aspects, the task comprises:

receiving a minimum duration over time corresponding to a maximum flow rate of the apparatus;

receiving a maximum duration over time corresponding to a minimum flow rate of the apparatus;

computing a duration over time interpolating curve based on the minimum duration over time, the maximum flow rate, the maximum duration over time, the minimum flow rate;

computing the duration over time through said duration over time interpolating curve.

In a 6th aspect according to the preceding aspect, the task further comprises:

receiving at least one mid duration over time corresponding to a mid flow rate of the apparatus, wherein the mid flow rate is comprised between the maximum flow rate and the minimum flow rate;

computing a duration over time interpolating curve based on the minimum duration over time, the maximum flow rate, the maximum duration over time, the minimum flow rate and the mid duration over time and the mid flow rate.

In a 7th aspect according to any one of the preceding aspects, the duration over time is computed using the mathematical formula:

$$\Delta T=((\Delta T_{min}-\Delta T_{max})/(Q\text{dial}_{max}-Q\text{dial}_{min}))*(Q\text{dial}-Q\text{dial}_{max})+\Delta T_{min}$$

where:

Qdial is the flow rate of the fresh treatment liquid in the preparation line (note that Qdial is the current set or actual flow rate of the fresh treatment liquid in the preparation line; Qdial is generally the flow rate of the fresh treatment liquid in the preparation line at the time the calculation is made);

$Qdial_{max}$ is a prefixed maximum flow rate of the fresh treatment liquid in the preparation line of the apparatus;

$\Delta T_{min}$ is a prefixed minimum duration over time corresponding to the maximum flow rate of the apparatus;

$Qdial_{min}$ is a prefixed minimum flow rate of the fresh treatment liquid in the preparation line of the apparatus;

$\Delta T_{max}$ is a prefixed maximum duration over time corresponding to the minimum flow rate of the apparatus.

In a further aspect according to any one of the preceding aspects, computing the amplitude is a function of a difference between a prefixed maximum flow rate of the fresh treatment liquid and a prefixed minimum flow rate of the fresh treatment liquid.

In a further aspect according to any one of the preceding aspects, computing the amplitude is a function of a prefixed maximum amplitude, in particular corresponding to a minimum flow rate of the apparatus. The prefixed maximum amplitude may be received from a memory or an input device of the apparatus, or may be calculated, based on e.g., an apparatus set-up.

In a further aspect according to any one of the preceding aspects, computing the amplitude is a function of a prefixed minimum amplitude, in particular corresponding to a maximum flow rate of the apparatus. The prefixed minimum amplitude may be received from a memory or an input device of the apparatus, or may be calculated, based on e.g., an apparatus set-up.

In a further aspect according to any one of the two preceding aspects, computing the amplitude is a function of a difference between the prefixed maximum amplitude and the prefixed minimum amplitude. In a further aspect according to the preceding aspect, computing the amplitude is a function of a ratio between the difference between the prefixed maximum amplitude and the prefixed minimum amplitude and the difference between a prefixed maximum flow rate of the fresh treatment liquid and a prefixed minimum flow rate of the fresh treatment liquid. In particular, the ratio being the multiplying factor.

In a further aspect according to any one of the preceding aspects, computing the amplitude includes a sum of a main term based on the flow rate of the fresh treatment liquid and an auxiliary term being an amplitude, in particular the amplitude being a prefixed minimum amplitude or a prefixed maximum amplitude.

In an 8th aspect according to any one of the preceding aspects, the task comprises:

- receiving a minimum amplitude corresponding to a maximum flow rate of the apparatus;
- receiving a maximum amplitude corresponding to a minimum flow rate of the apparatus;
- computing an amplitude interpolating curve based on the minimum amplitude, the maximum flow rate, the maximum amplitude, the minimum flow rate;
- computing the amplitude through said amplitude interpolating curve.

In a 9th aspect according to the preceding aspect, the task further comprises:

- optionally receiving at least one mid amplitude corresponding to a mid flow rate of the apparatus, wherein the mid flow rate is comprised between the maximum flow rate and the minimum flow rate;
- computing an amplitude interpolating curve based on the minimum amplitude, the maximum flow rate, the maximum amplitude, the minimum flow rate and, optionally, the mid amplitude and the mid flow rate.

In a 10th aspect according to any one of the preceding aspects, the amplitude is computed using the mathematical formula:

$$\Delta C_{in}=((\Delta C_{min}-\Delta C_{max})/(Q\mathrm{dial}_{max}-Q\mathrm{dial}_{min}))*(Q\mathrm{dial}-Q\mathrm{dial}_{max})+\Delta C_{min}$$

where:

- Qdial is the flow rate of the fresh treatment liquid in the preparation line;
- $\mathrm{Qdial}_{max}$ is a prefixed maximum flow rate of the fresh treatment liquid in the preparation line of the apparatus;
- $\Delta C_{min}$ is a prefixed minimum amplitude corresponding to the maximum flow rate of the apparatus;
- $\mathrm{Qdial}_{min}$ is a prefixed minimum flow rate of the fresh treatment liquid in the preparation line of the apparatus;
- $\Delta C_{max}$ is a prefixed maximum amplitude corresponding to the minimum flow rate of the apparatus.

In a 11th aspect according to any one of the preceding aspects, optionally the minimum flow rate of the apparatus is between 250 ml/min and 350 ml/min and, optionally, the maximum flow rate of the apparatus is between 750 ml/min and 850 ml/min and, optionally, the mid flow rate of the apparatus is between 500 ml/min and 600 ml/min.

In a 12th aspect according to any one of the preceding aspects, optionally the minimum duration over time corresponding to the maximum flow rate of the apparatus is between 80 s and 100 s and, optionally, the maximum duration over time corresponding to the minimum flow rate of the apparatus is between 140 s and 160 s and, optionally, the mid duration over time corresponding to the mid flow rate of the apparatus is between 110 s and 130 s.

In a 13th aspect according to any one of the preceding aspects, the characteristic is the conductivity in the fresh liquid and, optionally, the minimum amplitude corresponding to the maximum flow rate of the apparatus is between 0.4 mS/cm and 0.6 mS/cm and, optionally, the maximum amplitude corresponding to the minimum flow rate of the apparatus is between 0.9 mS/cm and 1.1 mS/cm and, optionally, the mid amplitude corresponding to the mid flow rate of the apparatus is between 0.7 mS/cm and 0.8 mS/cm.

In a 14th aspect according to any one of the preceding aspects, computing the amplitude and/or the duration over time comprises: selecting the amplitude and/or the duration over time among a plurality of fixed amplitudes and/or fixed durations over time stored in the control unit and each corresponding to a range which the received flow rate falls in.

In a 15th aspect according to the preceding aspect, said range is one of a plurality of ranges of flow rate stored in the control unit.

In a 16th aspect according any of the preceding aspects 1, 2, 14 or 15, said task comprises:

- receiving “n” fixed durations over time;
- receiving “n” ranges of the flow rate of the fresh treatment liquid, each of the “n” ranges being allocated to a fixed duration over time;

wherein computing the durations over time comprises:

- comparing the received flow rate with the “n” ranges;
- selecting the fixed duration over time corresponding to a range of said “n” ranges which the flow rate falls in.

In a 17th aspect according to the preceding aspect, the “n” fixed durations over time comprise:

- a first duration over time, optionally of 150 s;
- a second duration over time, optionally of 120 s;
- a third duration over time, optionally of 90 s.

In an 18th aspect according to any of the preceding aspects 1, 2, 14 to 17, said task comprises:

- receiving “n” fixed amplitudes;
- receiving “n” ranges of the flow rate of the fresh treatment liquid, each of the “n” being allocated to a fixed amplitude;

wherein computing the amplitude comprises:

- comparing the received flow rate with the “n” ranges;
- selecting the fixed amplitude corresponding to a range of said “n” ranges which the flow rate falls in.

In a 19th aspect according to preceding aspect, the “n” fixed amplitudes comprise:

- a first amplitude, optionally of 0.5 mS/cm;
- a second amplitude, optionally of 0.7 mS/cm;
- a third amplitude, optionally of 1 mS/cm.

In a 20th aspect according to any of the preceding aspects 16 to 19, the “n” ranges of the flow rate comprise:

- a first range, optionally between 300 and 400 ml/min;
- a second range, optionally between 400 and 650 ml/min;
- a third range, optionally between 650 and 800 ml/min.

In a 21st aspect according any of the preceding aspects, said task comprises: causing the upstream variation of the value of the characteristic such that the upstream variation of the value of the characteristic is all above or all below the prescription baseline and wherein said amplitude is a difference between the prescription baseline and a maximum or a minimum of the upstream variation.

In a 22nd aspect according to any one of the preceding aspects from 1 to 20, said task comprises: causing the upstream variation of the value of the characteristic such that the upstream variation of the value of the characteristic comprises at least one part above the prescription baseline and at least one part below the prescription baseline; the duration over time being a sum of partial durations over time of said at least one part above the prescription baseline and said at least one part below the prescription baseline; optionally, said amplitude being a difference between a maximum and a minimum of the upstream variation; optionally, said part/s above the prescription baseline and said part/s below the prescription baseline being arranged consecutively one after the other; optionally, said part/s above the prescription baseline being arranged alternately with said part/s below the prescription baseline.

In a 23rd aspect according to the preceding aspect, causing the upstream variation of the value of the characteristic such that a total area of the part or parts of the upstream variation of the value of the characteristic above the prescription baseline is equal to or substantially equal to a total area of the part or parts of the upstream variation of the value of the characteristic below the prescription baseline.

A 24th aspect concerns apparatus for extracorporeal treatment of blood comprising:

a blood treatment unit having a primary chamber and a secondary chamber separated by a semi-permeable membrane;

a preparation line having one end connected to an inlet of a secondary chamber of the treatment unit and configured to convey fresh treatment liquid to the secondary chamber, the fresh treatment liquid presenting a characteristic which is one selected in the group of:

- conductivity in the fresh treatment liquid, and
- concentration of at least one substance in the fresh treatment liquid, a spent dialysate line having one end connected to an outlet of said secondary chamber and configured to remove spent liquid from the secondary chamber, the spent liquid presenting a characteristic which is one selected in the group of:

- conductivity in the spent liquid, and
- concentration of at least one substance in the spent liquid, a control unit configured for commanding execution of a task for determination of a parameter indicative of the effectiveness of the extracorporeal blood treatment, said task comprising the following steps:

- receiving at least one prescription baseline for the characteristic in the fresh treatment liquid;
- causing fresh treatment liquid to flow in the preparation line to the secondary chamber with the characteristic being at said prescription baseline;
- causing spent liquid to flow out of the secondary chamber into the spent dialysate line;
- causing an upstream variation of the value of the characteristic in the fresh treatment liquid with respect to said prescription baseline thereby causing a corresponding and timely delayed downstream variation of the same characteristic in the spent liquid flowing in the spent dialysate line; wherein the upstream variation has an amplitude and a duration over time;
- computing at least one value of a parameter indicative of the effectiveness of the extracorporeal blood treatment by using values correlated to the upstream variation of the value of the characteristic in the fresh treatment liquid and to the downstream variation of the same characteristic in the spent liquid;

wherein said task comprises: causing the upstream variation of the value of the characteristic such that said upstream variation comprises at least one part above the prescription baseline and at least one part below the prescription baseline and such that a total area of the part or parts of the upstream variation above the prescription baseline is equal to or substantially equal to a total area of the part or parts of the upstream variation below the prescription baseline; optionally, said part/s above the prescription baseline and said part/s below the prescription baseline being arranged consecutively one after the other; optionally, said part/s above the prescription baseline being arranged alternately with said part/s below the prescription baseline.

In a 25th aspect according to any one of the preceding aspects 22 or 23 or 24, said task comprises:

- receiving a maximum allowed value of the characteristic in the fresh treatment liquid;
- receiving a minimum allowed value of the characteristic in the fresh treatment liquid;
- causing the upstream variation of the value of the characteristic such that said upstream variation is all between the minimum allowed value of the characteristic and the maximum allowed value of the characteristic.

In a 26th aspect according to anyone of the preceding aspects, the characteristic in the fresh treatment liquid is conductivity and optionally the maximum allowed conductivity absolute value is between 15 mS/cm and 16 mS/cm and optionally the minimum allowed conductivity absolute value is between 12 mS/cm and 13 mS/cm.

In a 27th aspect according to any one of the preceding aspects, said task comprises: causing the upstream variation of the value of the characteristic such that the upstream variation of the value of the characteristic or the parts of the upstream variation of the value of the characteristic has/have a rectangular or substantially rectangular shape or is/are bell-shaped or substantially bell-shaped.

In a 28th aspect according to any one of the preceding aspects, said task comprises the following steps:

- receiving at least one parametric mathematical model which puts into relation the characteristic in the fresh treatment liquid with the characteristic in the spent liquid, said parametric mathematical model presenting a prefixed number of free parameters;
- measuring a plurality of values taken by a reference portion of said downstream variation of the characteristic in the spent liquid, said reference portion having duration shorter than the entire duration of the downstream variation;
- estimating said free parameters of the at least one parametric mathematical model through said reference portion measured values and identifying one single characteristic mathematical model which puts into relation the characteristic in the fresh treatment liquid with the characteristic in the spent liquid;
- computing said at least one value of a parameter indicative of the effectiveness of the extracorporeal blood treatment by using said characteristic mathematical model and one or more values taken by the characteristic in the fresh treatment liquid.

In a 29th aspect according to the preceding aspect, said parameter comprises one selected in the group of:

- an effective dialysance for one or more substances of the treatment unit (D),
- an effective clearance for one or more substances of the treatment unit (K), a concentration of a substance in blood ($Cb_{in}$) upstream the blood treatment unit (2), a dialysis dose at time (t) after start of the treatment (K·t/V);

a plasma conductivity upstream the blood treatment unit (2).

A 30th aspect concerns a method for determining an effectiveness parameter which may be used in an apparatus for extracorporeal treatment of blood comprising:

a blood treatment unit having a primary chamber and a secondary chamber separated by a semi-permeable membrane;

a preparation line having one end connected to an inlet of a secondary chamber of the treatment unit and configured to convey fresh treatment liquid to the secondary chamber, the fresh treatment liquid presenting a characteristic which is either the conductivity in the fresh treatment liquid or the concentration of at least one substance (for instance sodium or calcium or potassium) in the fresh treatment liquid;

a spent dialysate line having one end connected to an outlet of said secondary chamber and configured to remove spent liquid from the secondary chamber, the spent liquid presenting a characteristic which is either the conductivity in the fresh treatment liquid or the concentration of at least one substance (for instance sodium or calcium or potassium) in the fresh treatment liquid;

wherein the method comprises:

causing an upstream variation of the value of the characteristic in the fresh treatment liquid with respect to a prescription baseline thereby causing a corresponding and timely delayed downstream variation of the same characteristic in the spent liquid flowing in the spent dialysate line; wherein the upstream variation has an amplitude and a duration over time;

computing at least one value of a parameter indicative of the effectiveness of the extracorporeal blood treatment by using values correlated to the upstream variation of the value of the characteristic in the fresh treatment liquid and to the downstream variation of the same characteristic in the spent liquid; optionally said values correlated to the upstream variation and values correlated to the downstream variation being measured and/or computed;

wherein said amplitude and/or said duration over time of the upstream variation to be caused are/is computed as a function of a flow rate of the fresh treatment liquid or of the parameter correlated to said flow rate.

In a 31st aspect according to the preceding aspect, the method comprises:

using at least one parametric mathematical model which puts into relation the characteristic in the fresh treatment liquid with the characteristic in the spent liquid, said parametric mathematical model presenting a prefixed number of free parameters;

measuring a plurality of values taken by a reference portion of said downstream variation of the characteristic in the spent liquid, said reference portion having duration shorter than the entire duration of the downstream variation;

estimating said free parameters of the at least one parametric mathematical model through said reference portion measured values and identifying one single characteristic mathematical model which puts into relation the characteristic in the fresh treatment liquid with the characteristic in the spent liquid;

computing at least one value of a parameter indicative of the effectiveness of the extracorporeal blood treatment by using said characteristic mathematical model and one or more values taken by the characteristic in the fresh treatment liquid.

The method of the 30th and 31st aspects may be used adopting the apparatus of any one of aspects from the 1st to the 29th.

DESCRIPTION OF THE DRAWINGS

Aspects of the invention are shown in the attached drawings, which are provided by way of non-limiting example, wherein.

DETAILED DESCRIPTION

Figure 1:
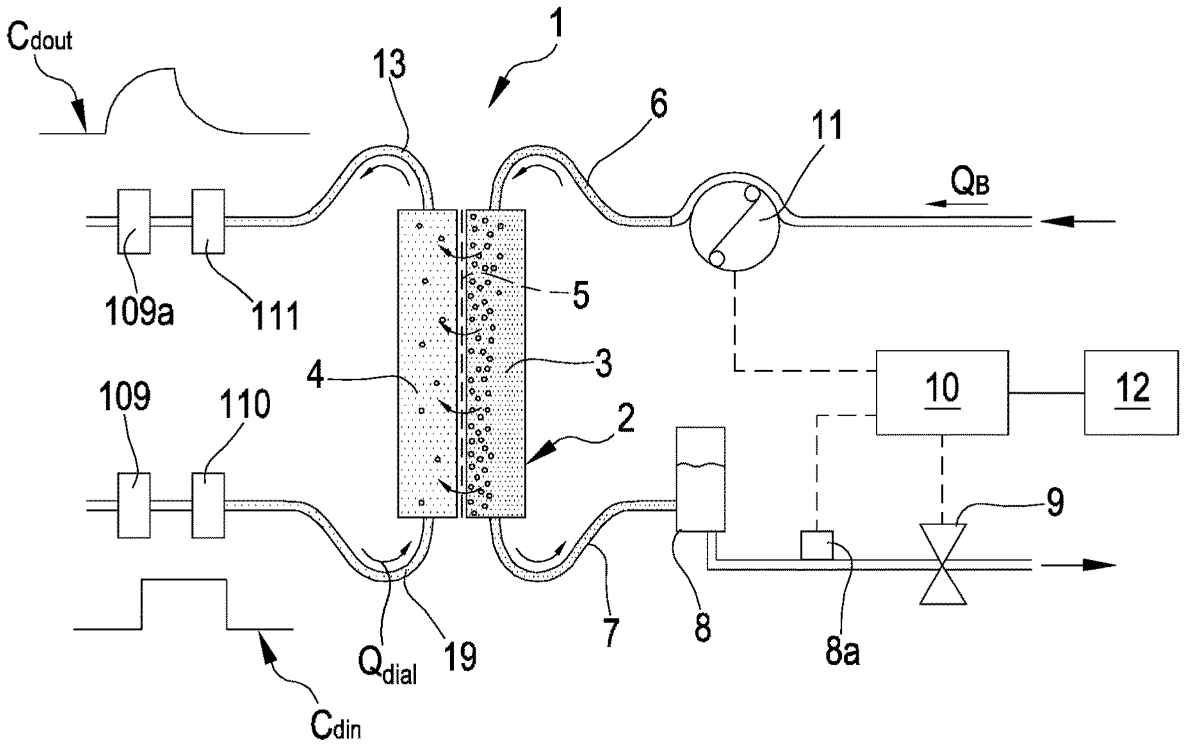
FIG. 1 shows a schematic diagram of a blood treatment apparatus according to one aspect of the invention.
Figure 2:
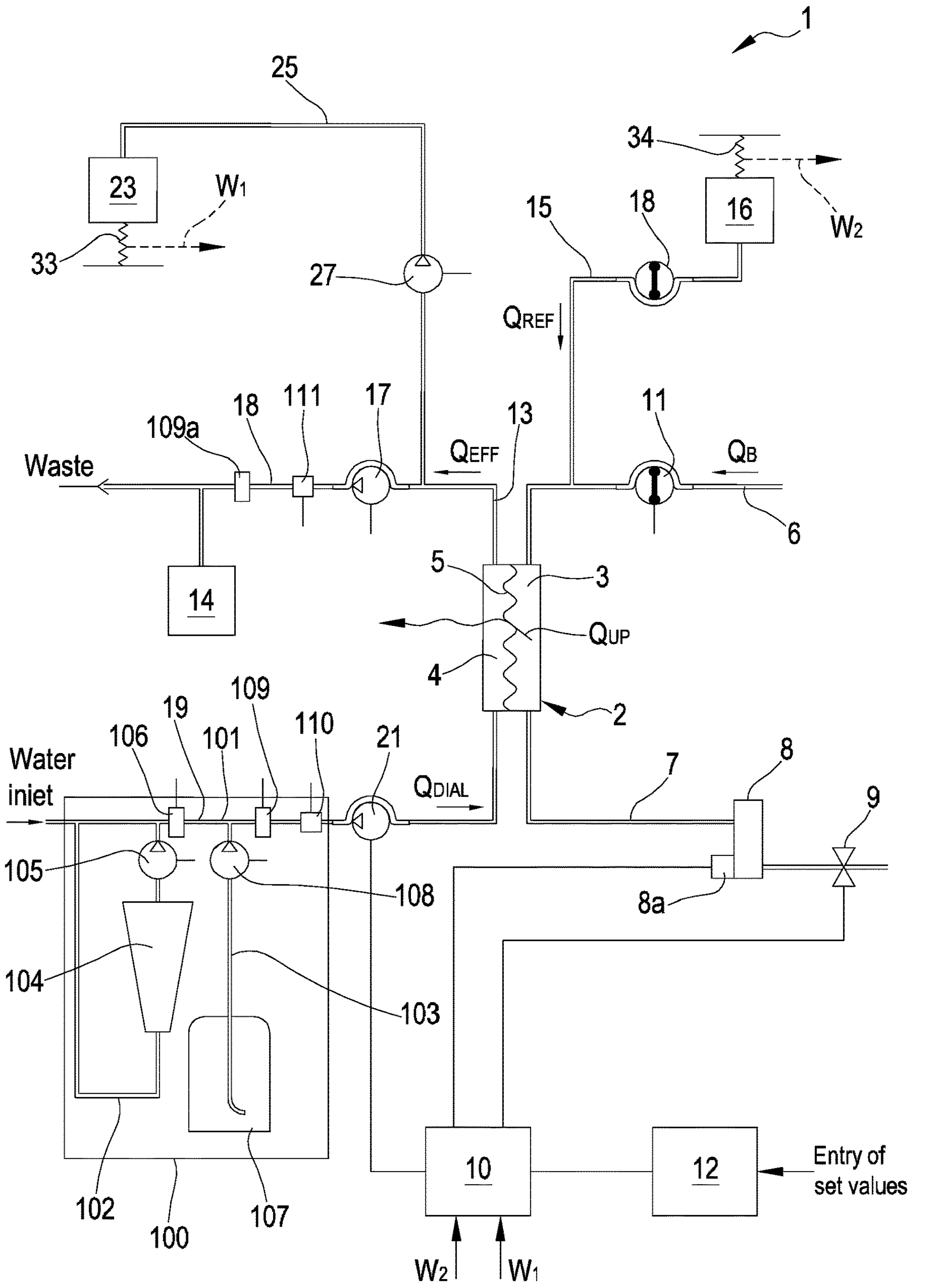
FIG. 2 shows a schematic diagram of an alternative embodiment of a blood treatment apparatus according to another aspect of the invention.
Figure 3:
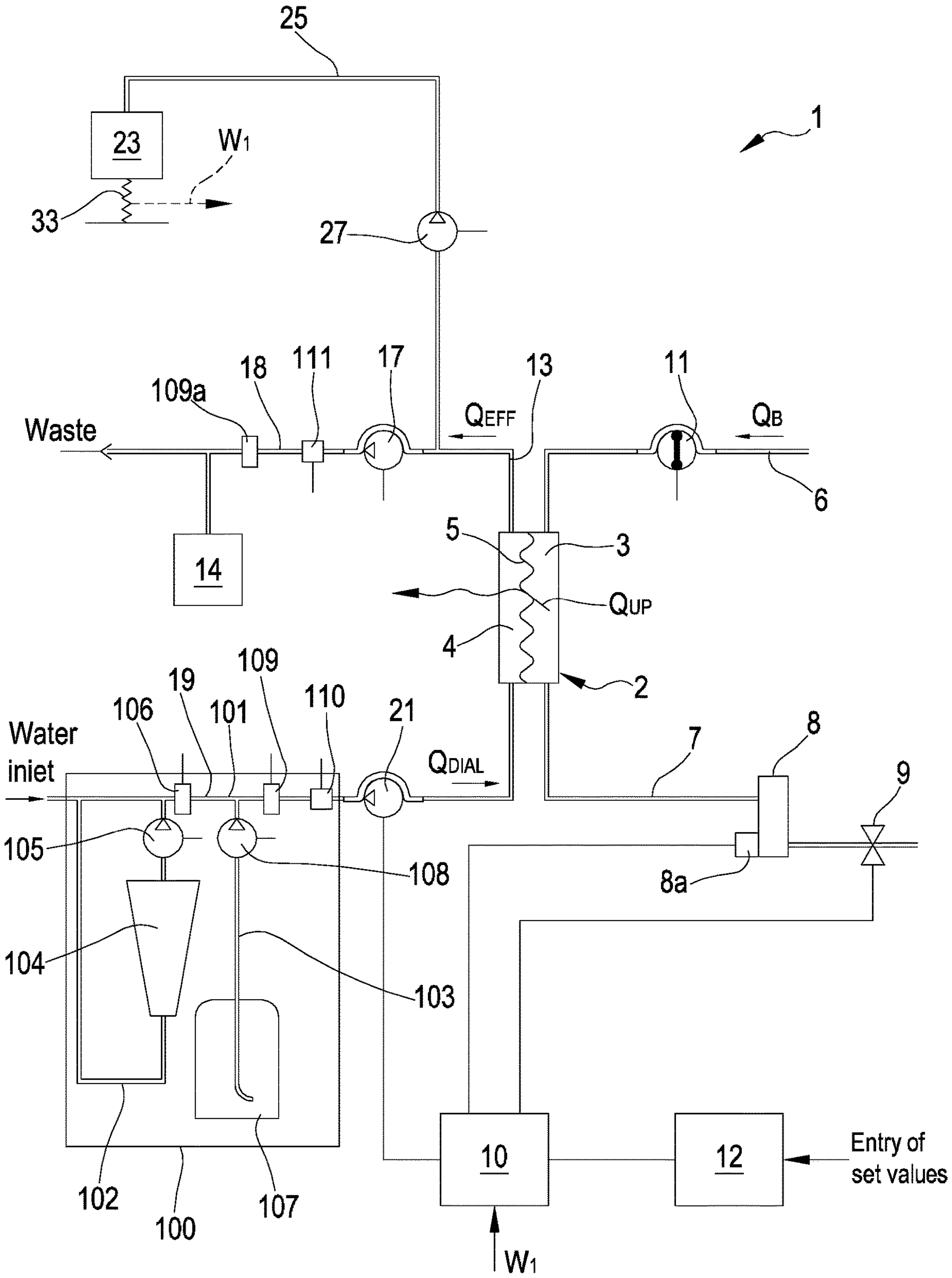
FIG. 3 shows a schematic diagram of another alternative embodiment of a blood treatment apparatus according to a further aspect of the invention.

Non-limiting embodiments of an apparatus 1 for extracorporeal treatment of blood—which may implement innovative aspects of the invention—are shown in FIGS. 1 to 3. FIG. 1 is a more schematic representation of the extracorporeal blood treatment apparatus 1, while FIGS. 2 and 3 represent, in greater detail, two possible non limiting embodiments of the apparatus 1.

The apparatus 1 may be configured to determine a parameter indicative of the effectiveness of the treatment delivered to a patient (here below also referred to as effectiveness parameter). The effectiveness parameter may be one of the following:

- an effective dialysance for one or more substances of the treatment unit (D), e.g. electrolyte or sodium clearance;
- an effective clearance for one or more substances of the treatment unit (K), e.g. urea clearance;
- a concentration of a substance in blood ($Cb_{in}$) upstream the blood treatment unit, e.g. sodium concentration in the blood upstream the treatment unit;
- a plasma conductivity upstream the blood treatment unit;
- a dialysis dose delivered until a certain point in time after start of the treatment (K·t/V), where K is clearance, t represents the time interval from start of treatment until the point in time, and V represents a reference volume characteristic of the patient.

Note that a parameter proportional to one of the above parameters or known function of one or more of the above parameters may alternatively be used as 'effectiveness' parameter.

Figure 7:
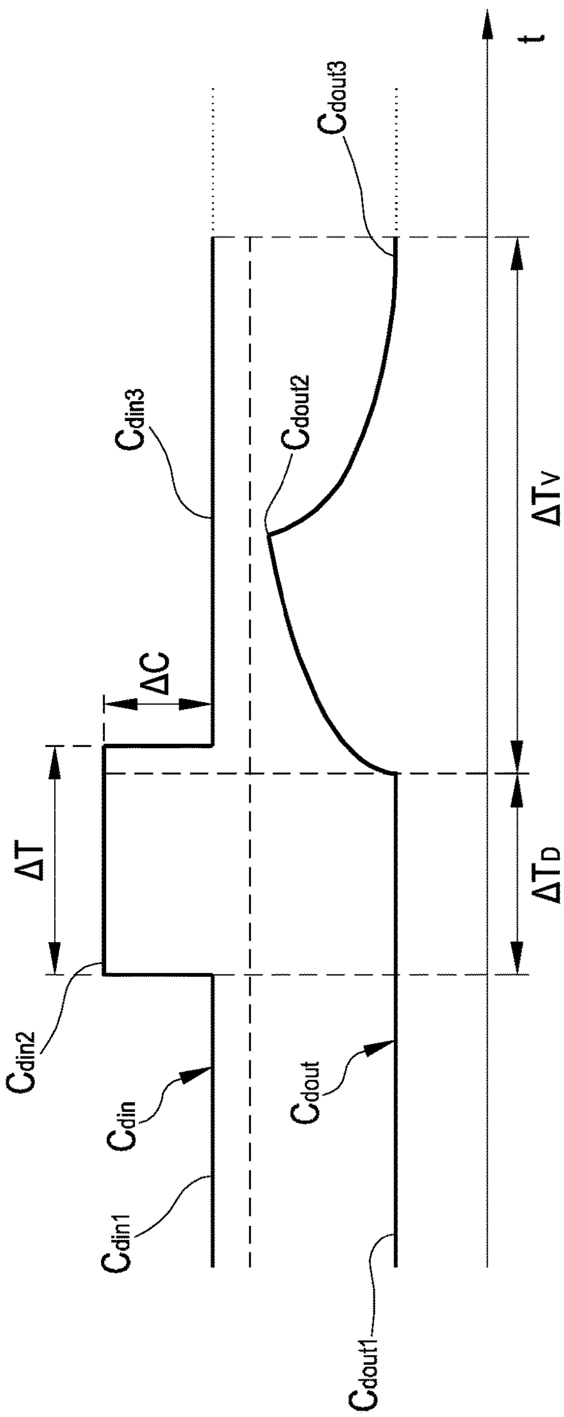
FIGS. 7 and 8 show a conductivity (or concentration) vs. time diagram in the fresh and in the spent dialysate line wherein the conductivity (or concentration) variation in the fresh dialysate line is in the form of a relatively short step.

In below description and in FIGS. 1 to 3 same components are identified by same reference numerals. In FIG. 1 it is represented an apparatus for the extracorporeal treatment of blood 1 comprising a treatment unit 2 (such as an hemofilter, an ultrafilter, an hemodiafilter, a dialyzer, a plasmafilter and the like) having a primary chamber 3 and a secondary chamber 4 separated by a semi-permeable membrane 5; depending upon the treatment, the membrane of the filtration unit may be selected to have different properties and performances. A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. An air separator, such as a bubble trap 8, may be present on the blood return line; moreover, a safety clamp 9 controlled by a control unit 10 may be present on the blood return line downstream the bubble trap 8. A bubble sensor 8*a*, for instance associated to the bubble trap 8 or coupled to a portion of the line 7 between bubble trap 8 and clamp 9 may be present: if present, the bubble sensor is connected to the control unit 10 and sends to the control unit 10 signals for the control unit 10 to cause closure of the clamp 9 in case one or more bubbles above certain safety thresholds are detected. The blood flow through the blood lines is controlled by a blood pump 11, for instance a peristaltic blood pump, acting either on the blood withdrawal line or on the blood return line. An operator may enter a set value for the blood flow rate $Q_B$ through a user interface 12 and the control unit 10, during treatment, is configured to control the blood pump based on the set blood flow rate $Q_B$. The control unit 10 may comprise a digital processor (CPU) and a memory (or memories), an analogical type circuit, or a combination thereof as explained in greater detail in below section dedicated to the 'control unit 10'. An effluent fluid line or spent dialysate line 13 is connected, at one end, to an outlet of the secondary chamber 4 and, at its other end, to a waste which may be a discharge conduit or an effluent fluid container collecting the fluid extracted from the secondary chamber. A fresh dialysis fluid line 19 is connected to the inlet of the secondary chamber 4 and supplies fresh dialysate to from a source to said second chamber. Conductivity or concentration sensors 109, 109*a* are respectively positioned on the fresh dialysis fluid line 19 and on the spent dialysate line 13. Concentration or conductivity sensor 109 is configured for detecting the conductivity or the concentration for one substance of for a group of substances—identified as $Cd_{in}$—in the fresh dialysis fluid line 19. Concentration or conductivity sensor 109*a* is configured for detecting the conductivity or the concentration for one substance of for a group of substances—identified as $Cd_{out}$—in the spent dialysate line 13. FIG. 2 shows an apparatus 1 configured to deliver any one of treatments like ultrafiltration and hemodialysis and hemodiafiltration. The apparatus of FIG. 2 comprises all the features described above in connection with FIG. 1, which are identified in FIG. 2 with same reference numerals. Furthermore, in the apparatus of FIG. 2, other features of a possible embodiment of the apparatus 1 are schematically shown: an effluent fluid pump 17 that operates on the effluent fluid line under the control of control unit 10 to regulate the flow rate $Q_{eff}$ across the effluent fluid line. The apparatus 1 may also include an ultrafiltration line 25 branching off the effluent line 13 and provided with a respective ultrafiltration pump 27 also controlled by control unit 10. The embodiment of FIG. 2 presents a pre-dilution fluid line 15 connected to the blood withdrawal line: this line 15 supplies replacement fluid from an infusion fluid container 16 connected at one end of the pre-dilution fluid line. Although in FIG. 2 a container 16 is shown as the source of infusion fluid, this should not be interpreted in a limitative manner: indeed, the infusion fluid may also come from an on line preparation section 100 part of the apparatus 1. Note that alternatively to the pre-dilution fluid line 15 the apparatus of FIG. 1 may include a post-dilution fluid line (not shown in FIG. 2) connecting an infusion fluid container to the blood return line. Finally, as a further alternative (not shown in FIG. 2) the apparatus of FIG. 2 may include both a pre-dilution and a post infusion fluid line: in this case each infusion fluid line may be connected to a respective infusion fluid container or the two infusion fluid lines may receive infusion fluid from a same source of infusion fluid such as a same infusion fluid container. Once again, the source of infusion fluid may alternatively be an online preparation section part of the apparatus 1 (similar to the device 100 described herein below) supplying fluid to the post and/or pre dilution lines. Furthermore, an infusion pump 18 operates on the infusion line 15 to regulate the flow rate $Q_{rep}$ through the infusion line. Note that in case of two infusion lines (pre-dilution and post-dilution) each infusion line may be provided with a respective infusion pump. The apparatus of FIG. 2 includes a dialysis fluid line 19 connected at one end with a water inlet and at its other end with the inlet of the secondary chamber 4 of the filtration unit for supplying fresh dialysis liquid to the secondary chamber 4. A dialysis fluid pump 21 is operative on the dialysis liquid fluid line 19 under the control of said control unit 10, to supply fluid from the dialysis liquid container to the secondary chamber at a flow rate Qdial. The dialysis fluid pump 21, the ultrafiltration pump 27, the concentrate pumps 105 and 108, the infusion fluid pump 15 and the effluent fluid pump 17 are operatively connected to the control unit 10 which controls the pumps as it will be in detail disclosed herein below. An initial tract of line 19 links the haemodialyser or hemodiafilter 2 to a device 100, for preparing the dialysis liquid, which also includes a further tract of said line 19. The device 100 comprises a main line 101, the upstream end of which is designed to be connected to a supply of running water. Connected to this main line 101 are a first secondary line 102 and a second secondary line 103. The first secondary line 102, which may be looped back onto the main line 101, is provided with a connector configured for fitting a container 104, such as a bag or cartridge or other container, containing sodium bicarbonate in granule form (alternatively a concentrate in liquid form may be used). Line 102 is furthermore equipped with a concentrate pump 105 for metering the sodium bicarbonate into the dialysis liquid: as shown in FIG. 7 the pump may be located downstream of the container 104. The operation of the pump 105 is determined by the comparison between 1) a conductivity set point value for the solution forming at the junction of the main line 101 and the first secondary line 102 and 2) the value of the conductivity of this mixture measured through a first conductivity probe 106 located in the main line 101 immediately downstream of the junction between the main line 101 and the first secondary line 102. The free end of the second secondary line 103 is intended to be immersed in a container 107 for a concentrated saline solution, e.g. containing sodium chloride, calcium chloride, magnesium chloride and potassium chloride, as well as acetic acid. The second secondary line 103 is equipped with a pump 108 for metering sodium into the dialysis liquid, the operation of which pump depends on the comparison between 1) a second conductivity set point value for the solution forming at the junction of the main line 101 and the second secondary line 103 and 2) the value of the conductivity of this solution measured through a second conductivity probe 109 located in the main line 12 immediately downstream of the junction between the main line 12 and the secondary line 103. Note that as an alternative, instead of conductivity sensors concentration sensors may in principle be used. Moreover, the specific nature of the concentrates contained in containers 104 and 107 may be varied depending upon the circumstances and of the type of dialysis fluid to be prepared. The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof. The embodiment of FIG. 3 shows an alternative apparatus 2 designed for delivering any one of treatments like hemodialysis and ultrafiltration. The apparatus of FIG. 3 includes the same components described for the apparatus of FIG. 1. In the apparatus shown in FIG. 3 the same components described for the embodiment of FIG. 2 are identified by same reference numerals and thus not described again. In practice, differently from the hemodiafiltration apparatus of FIG. 2, the apparatus of FIG. 3 does not present any infusion line. In each one of the above described embodiments, flow sensors 110, 111 (either of the volumetric or of the mass type) may be used to measure flow rate in each of the lines. Flow sensors are connected to the control unit 10. In the example of FIG. 2 where the infusion line 15 and the ultrafiltration line 25 lead to a respective bag 16, 23, scales may be used to detect the amount of fluid delivered or collected. For instance, the apparatus of FIG. 2 includes a first scale 33 operative for providing weight information $W_1$ relative to the amount of the fluid collected in the ultrafiltration container 23 and a second scale 34 operative for providing weight information $W_2$ relative to the amount of the fluid supplied from infusion container 16. In the embodiment of FIG. 3, the apparatus includes a first scale 33 operative for providing weight information $W_1$ relative to the amount of the fluid collected in the ultrafiltration container 23. The scales are all connected to the control unit 10 and provide said weight information $W_1$ for the control unit 10 to determine the actual quantity of fluid in each container as well as the actual flow rate of fluid supplied by, or received in, each container. In the example of FIG. 1 there is no dedicated ultrafiltration line and the total amount of ultrafiltration is determined by the difference of the flow rates detected by sensors 110 and 111. The control unit 10 is configured to act on appropriate actuators, such as pumps, present on lines 13 and 19 and—using the information concerning the difference of flow rates as detected by sensors 110, 111—to make sure that a prefixed patient fluid removal is achieved in the course of a treatment time T, as required by the prescription provided to the control unit 10, e.g. via user interface 12. In the example of FIGS. 2 and 3, in order to control the fluid balance between the quantity of fluid supplied to the secondary chamber 4 and the quantity of fluid extracted from the secondary chamber, the flow-meters 110, 111 positioned on the fresh dialysate line and on the waste line 13 provide the control unit 10 with signals indicative of the flow of fluid through the respective lines and the scale or scales provide weight information which allow the control unit 10 to derive the flow rate through the ultrafiltration line 25 and, if present, through the infusion line 15. The control unit 10 is configured to control at least pumps 17, 21 and 27 (in case of FIG. 2 also pump 18) to make sure that a prefixed patient fluid removal is achieved in the course of a treatment time T, as required by the prescription provided to the control unit 10, e.g. via user interface 12. Note that other fluid balance systems may be used: for instance in case the apparatus includes a container as source of fresh dialysis fluid and a container to collect waste, then scales may be used to detect the amount of fluid delivered or collected by each container and then inform the control unit 10 accordingly. As a further alternative, systems based on volumetric control may be used where the fresh dialysis liquid line 19 and the waste line 13 are connected to a balance chamber system assuring that—at each instant—the quantity of liquid flowing into line 19 is identical to the quantity of fluid exiting from line 13. From a structural point of view one or more, containers/bags 104, 107, 14, 16, 23 may be disposable plastic containers. The blood lines 6, 7 lines and the filtration unit may also be plastic disposable components which may be mounted at the beginning of the treatment session and then disposed of at the end of the treatment session. Pumps, e.g. peristaltic pumps or positive displacement pumps, have been described as means for regulating fluid flow through each of the lines; however, it should be noted that other flow regulating means may alternatively be adopted such as for example valves or combinations of valves and pumps. The scales may comprise piezoelectric sensors, or strain gauges, or spring sensors, or any other type of transducer able to sense forces applied thereon. As already explained, the conductivity sensors may be replaced by concentration sensors.

Determination of the Effectiveness Parameter

As mentioned at the beginning of the detailed description, the apparatus 1 is capable of determining an effectiveness parameter. In this regard, the control unit 10 of the apparatus 1 is configured for commanding execution of a number of procedures including a task specifically devoted to the determination of the parameter indicative of the effectiveness of the extracorporeal blood treatment. The task devoted to determination of the effectiveness parameter comprises the steps described herein below. First, the control unit 10 is configured for receiving at least one prescription baseline $Cd_{set}$ for the characteristic $Cd_{in}$ in the fresh treatment liquid; the characteristic may be the concentration for one substance in the dialysis liquid (e.g. the sodium concentration, or the calcium concentration), or the concentration for a group of substances in the dialysis liquid (such as the electrolyte concentration) or the conductivity of the dialysis liquid. Furthermore, the set value for the prescription baseline may be either pre set in a memory connected to the control unit 10 or, alternatively, it may be entered by the user via user interface 12. Although the prescription baseline is frequently a constant value, it may alternatively comprise a time-variable value which changes during treatment according to a prefixed law. The control unit 10, acting on appropriate actuators such as pumps 21 and 17, causes circulation of dialysis fluid through lines 19 and 13 and through the secondary chamber 4 of the treatment unit 2. In greater detail, the control unit 10 is configured for causing fresh treatment liquid to flow in the preparation line 19 to the secondary chamber 4 with the characteristic being at said prescription baseline $Cd_{set}$: the characteristic at the baseline value may for instance be achieved by appropriately controlling the concentrate pumps 105, 108 of the preparation section 100. Furthermore, the control unit 10 is configured for reading the value of the characteristic through the spent dialysis fluid using sensor 109*a*. Depending upon the case, sensor 109*a* may for instance be a conductivity sensor, or a concentration sensor (sensitive to one or more substances).

Figure 4:
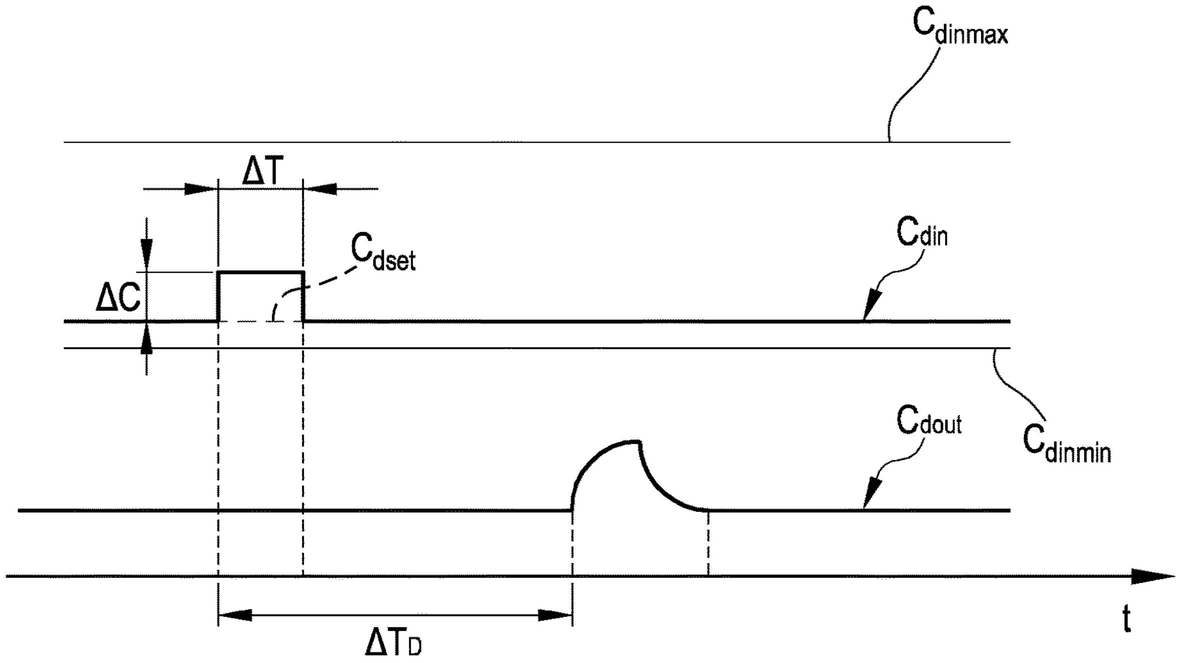
FIG. 4 shows a conductivity (or concentration) vs. time diagram showing the conductivity (or concentration) profile in the fresh and in the spent dialysate line, according to another aspect of the invention.

In addition to command the circulation of dialysis liquid in lines 19 and 13, the control unit 10, e.g. by acting one or more concentrate pumps 105, 108, causes an upstream variation of the value of the characteristic $Cd_{in}$ in the fresh treatment liquid with respect to said prescription baseline $Cd_{set}$ and then re-establishes the characteristic $Cd_{in}$ in the fresh treatment liquid to said prescription baseline $Cd_{set}$. Note that the alteration of the characteristic may be made using any means able to momentarily change the characteristic of the dialysis liquid, e.g. the conductivity or the concentration for one or more substances in the fresh dialysis fluid: for instance, a bolus pump configured to inject a predefined bolus of saline may be used for this purpose. The upstream variation causes a corresponding and timely delayed downstream variation of the same characteristic $Cd_{out}$ in the spent liquid flowing in the spent dialysate line: FIG. 4 schematically shows the time delay $\Delta T_D$ between the upstream variation and the downstream variation; the time delay which is also referred to as hydraulic delay depends upon the components such as tubing and second chamber interposed between the sensor 109 and the sensor 109*a*. The time delay $\Delta T_D$ between the upstream variation and the downstream variation is also shown in FIGS. 5, 6, 7, 8.

Parametric Mathematical Model

The control unit 10 is also configured to receive at least one parametric mathematical model which puts into relation the characteristic $Cd_{in}$ in the fresh treatment liquid with the characteristic $Cd_{out}$ in the spent liquid. The parametric mathematical model, which mathematically describes the components interposed between the two sensors 109, 109*a*, may for instance be pre-stored in a memory connected to the control unit 10, or it may be transferred to said memory via user interface 12 or via other input means such as a data reader, or it may be remotely transmitted from a remote source. The parametric model mathematically models the portion of hydraulic circuit between the sensors 109 and 109*a* and presents a prefixed number of free parameters that are determined as described herein below in order to characterize the parametric mathematical model into one single model. In practice, the parametric mathematical model defines a family of mathematical models and is univocally characterized only once the parameters of the model are determined.

Figure 5:
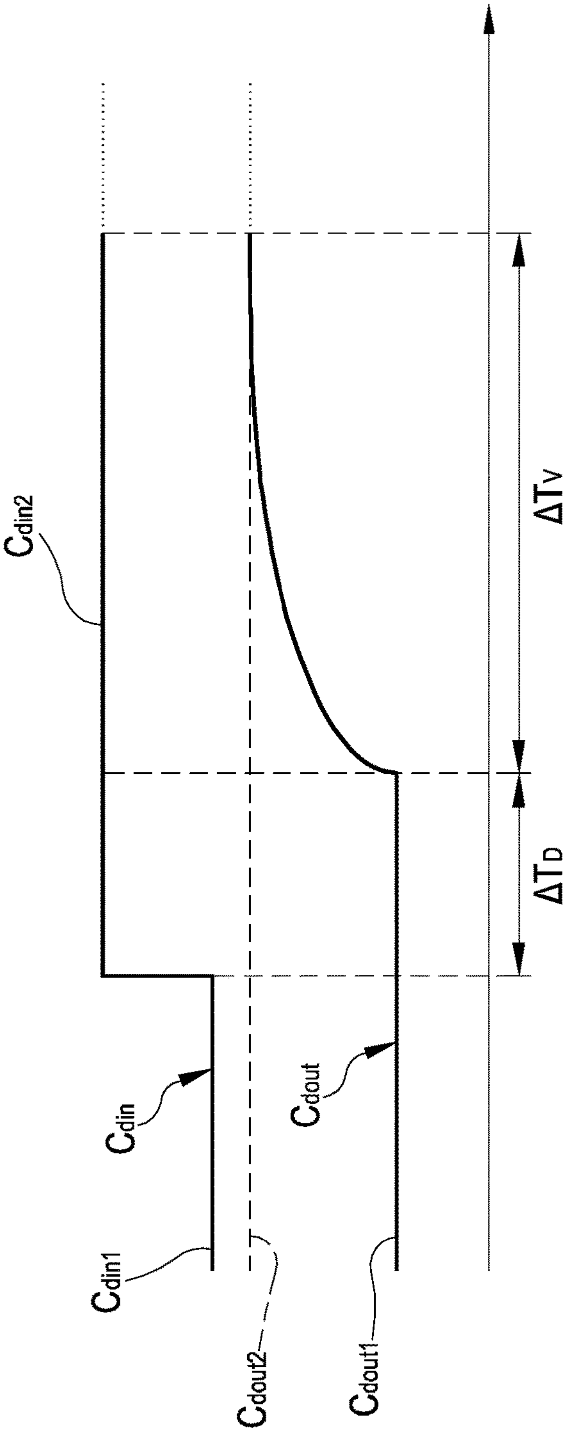
FIGS. 5 and 6 show a conductivity (or concentration) vs. time diagram in the fresh and in the spent dialysate line wherein the conductivity (or concentration) variation in the fresh dialysate line is in the form of a relatively long step.
Figure 6:
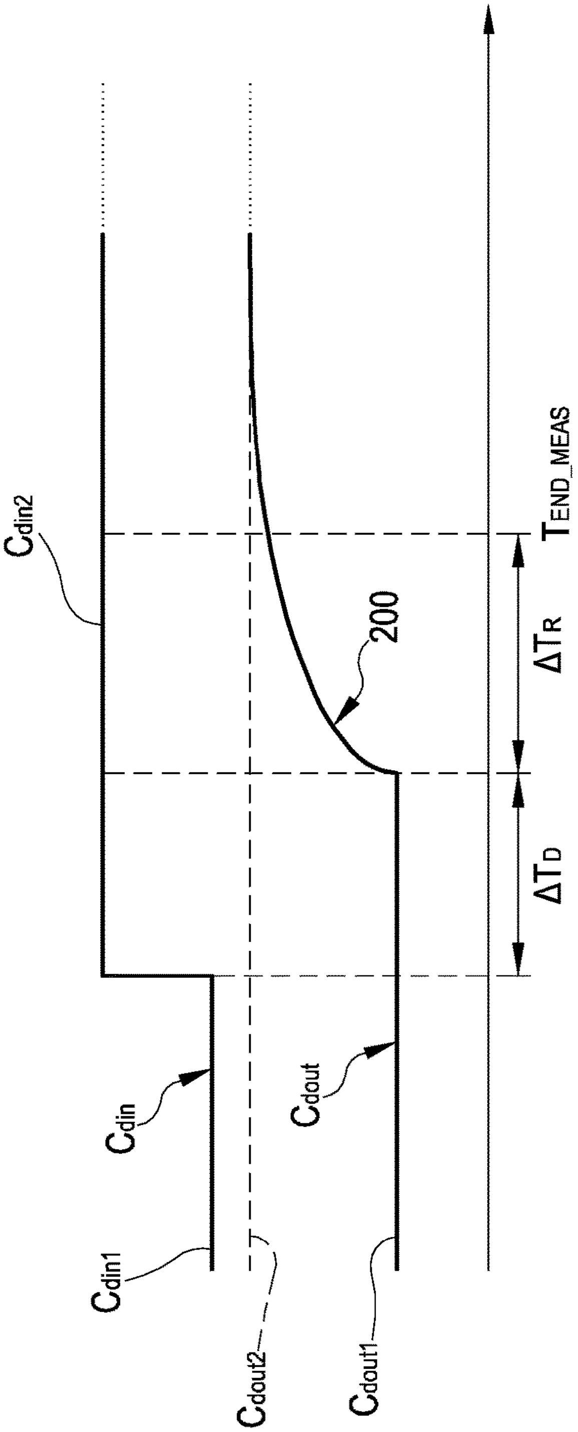

In order to determine the parameters of the parametric mathematical model, the control unit 10 is configured to receive, e.g. from sensor 109*a*, measures of a plurality of values taken by a reference portion 200 of the downstream variation of the characteristic $Cd_{out}$ in the spent liquid. The measured values taken by the reference portion 200 of the variation in the characteristic $Cd_{out}$ may be measured by first identifying the initiation of a ramp-up or of a ramp-down portion of the downstream variation with respect to a respective baseline value of the same characteristic $Cd_{out}$ in the spent liquid, and then by measuring the plurality of values, as values taken by said ramp-up portion or ramp-down portion of said downstream variation. According to an aspect of the invention, the reference portion 200 which is used by the control unit 10 to characterize the mathematical model has a duration $\Delta T_R$ significantly shorter than the entire duration $\Delta T_V$ of the downstream variation: duration $\Delta T_R$ may be less than 70% and optionally less than 50% of duration $\Delta T_V$. This is visible e.g. in FIGS. 5 and 6: FIG. 5 shows the duration $\Delta T_V$ of the entire downstream variation which certain conventional systems have to wait in order to calculate the effectiveness parameter, while FIG. 6 shows the much shorter interval $\Delta T_R$ necessary to characterize the mathematical model and then calculate the effectiveness parameter. More in detail, according to an aspect of the invention, the control unit 10 characterizes the mathematical model without having to wait for the entire interval $\Delta T_V$ by estimating the free parameters of the parametric mathematical model using measured values taken by the reference portion thereby identifying one single characteristic mathematical model using measured values taken during time interval $\Delta T_R$ which is much shorter than $\Delta T_V$. Once the parameters of the model have been determined, the control unit 10 has the characteristic mathematical model and may compute the value of the effectiveness parameter supplying as input to the characteristic mathematical model one or more values taken by the characteristic $Cd_{in}$ in the fresh treatment liquid. In other words with use of the parametric mathematical model and with the characterization of the same through measured values taken by the characteristic $Cd_{out}$ during $\Delta T_R$, it is possible to then calculate the effectiveness parameter with no need to take measures during the entire downstream variation, thus shortening the time during which control of the characteristic (e.g. concentration or conductivity of the dialysis liquid) should not be taken over by procedures other than the task for the determination of the effectiveness parameter. In other words the task for determining the effectiveness parameter should prevent execution of other procedures acting on the characteristic of the fresh dialysis liquid only until the end measurement instant $T_{END\_MEAS}$ represented in FIGS. 6, 8 and 9 which is the instant at which the measurement of said plurality of values of the reference portion of said downstream variation necessary for characterizing the model has been completed. In order to calculate the effectiveness parameter, the control unit 10 may for instance first compute at least one significant value of said downstream variation of the characteristic $Cd_{out}$: the significant value of the downstream variation is a computed not measured value which, as shown in the example of FIG. 6, relates to a time subsequent to the duration of the reference portion, for instance it may represent an asymptotic value $Cd_{out2}$ that the downstream variation would take after a relatively long time. This value is computed by using the characteristic mathematical model providing one or more real or set values representative of the upstream variation; once the significant value $Cd_{out2}$ has been determined, the control unit 10 may compute at least one value of a parameter (D, $Cb_{in}$, K, K·t/V) indicative of the effectiveness of the extracorporeal blood treatment from said computed significant value and from one or more values taken by the characteristic $Cd_{in}$ in the fresh treatment liquid.

The computation of the at least one significant value or directly of the effectiveness parameter comprises determining the value $Cd_{out}(n)$ of characteristic $Cd_{out}$ in the spent liquid at time instant (n) by using as input to the mathematical model:

a) the measured values of characteristic $Cd_{in}$ in the fresh treatment liquid at a plurality of time instants (n−1, n−2, n−3) preceding in time the time instant (n), as measured for instance by sensor 109; or b) a mathematically calculated version of characteristic $Cd_{in}$ in the fresh treatment liquid; in this second case the input is a set curve or a number of set values which are fed as input to the mathematical model.

The mathematical model—for instance a time invariant linear (LTI) model—may be represented in the time domain by the following recursive equation:

$$y(n)=a_0\cdot u(n)+b_1\cdot y(n-1)+b_2\cdot y(n-2)+\ldots b_m\cdot y(n-m),$$

Thus, the value $Cd_{out}(n)$ of characteristic $Cd_{out}$ in the spent liquid at time instant (n) subsequent to said reference portion is calculated with the following recursive equation:

$$Cd_{out}(n)=a_0\cdot Cd_{in}(n)+b_1\cdot Cd_{out}(n-1)+b_2\cdot Cd_{out}(n-2)+\ldots b_m\cdot Cd_{out}(n-m),$$

wherein:

$Cd_{out}(n)$ is the calculated value of the outlet characteristic at time instant (n), $Cd_{in}(n)$ is the known value of the inlet characteristic at time instant (n), $Cd_{out}(n-1)$, $Cd_{out}(n-2)$, . . . , $Cd_{out}(n-m)$ are values of the outlet characteristic at preceding time instants (n−1, n−2, . . . n−m) prior to time instant (n) and recursively computed through the mathematical model. $a_0$, $b_1$, $b_2$, . . . , $b_m$ are constant parameters that characterize the mathematical model, as estimated by using said measured values of the reference portion of the downstream variation.

In the frequency domain and using the z-Transform—the mathematical model is described by a transfer function H(z) having at least one zero and at least one pole. In an embodiment, the transfer function H(z) comprises a plurality of poles, e.g. from 2 to 5 poles, and is described by one of the following:

$$H(z)=Cd_{out}(z)/Cd_{in}(z)=a_0/(1-b_1\cdot z^{-1}-b_2\cdot z^{-2}-b_3\cdot z^{-3}-b_4\cdot z^{-4}-b_5\cdot z^{-5}),$$

$$H(z)=Cd_{out}(z)/Cd_{in}(z)=a_0/(1-b_1\cdot z^{-1}-b_2\cdot z^{-2}-b_3\cdot z^{-3}\cdot b_4\cdot z^{-4}),$$

$$H(z)=Cd_{out}(z)/Cd_{in}(z)=a_0/(1-b_1\cdot z^{-1}-b_2\cdot z^{-2}-b_3\cdot z^{-3}),$$

$$H(z)=Cd_{out}(z)/Cd_{in}(z)=a_0/(1-b_1\cdot z^{-1}-b_2\cdot z^{-2}),$$

wherein $a_0$, $b_1$, $b_2$, $b_3$, $b_4$, $b_5$ are constant parameters of the model, as estimated by using said measured values of the reference portion of the downstream variation.

FIGS. 5, 6 and 7, 8 respectively show two possible implementations of the invention. In FIGS. 5 and 6 the characteristic is altered from a first to a second value and kept at the second value for a relatively long time, while in FIGS. 7 and 8 the characteristic is kept at the second value for a relatively short time. More in detail, in the example of FIGS. 5 and 6, the value of the characteristic $Cd_{in}$ in the fresh treatment liquid is varied by imposing a change of the same from a first inlet value $Cd_{in1}$ to a second inlet value $Cd_{in2}$, which may be kept constant for a prefixed time interval of e.g. 3 to 10 minutes, thereby causing a corresponding change of the characteristic $Cd_{out}$ in spent liquid from a respective first outlet value $Cd_{out1}$ to a respective second outlet value $Cd_{out2}$ defining said timely delayed downstream variation of the characteristic $Cd_{out}$. In the example of FIGS. 5 and 6, the reference portion of the downstream variation begins after the characteristic in the spent liquid changes from said first outlet value $Cd_{out1}$ and lasts a period—for instance prefixed period $\Delta T_R$—during which the characteristic either continuously increases or decreases without reaching the second outlet value $Cd_{out2}$. In the example shown, during $\Delta T_R$ the characteristic $Cd_{out}$ does not reach a prefixed fraction, e.g. 80%, of the second outlet value $Cd_{out2}$. Moreover, there is no need to wait until the real value $Cd_{out2}$ is actually reached. Instead, the second outlet value $Cd_{out2}$ of the characteristic $Cd_{out}$ is calculated by using as input to the characteristic mathematical model the values of characteristic $Cd_{in}$ in the fresh treatment liquid, or a mathematically calculated version of the characteristic $Cd_{in}$ in the fresh treatment liquid.

Notably, a different mathematical model and approach may be used to determine the second outlet value $Cd_{out2}$.

Indeed, the response in the spent dialysate (effluent) line to the conductivity step, may be the input for the differential evolution algorithm that uses a mathematical model to predict the system response at the steady state. The differential evolution algorithm is an alternative method that optimizes the problem by iteratively trying to improve a candidate solution with regard to a given measure of quality. Such method is commonly known as metaheuristic as it makes few or no assumptions about the problem being optimized and can search very large spaces of candidate solutions. It has been proved from practical evidences that running a differential evolution algorithm for about 1000 generations provides a meaningful result for the second outlet value $Cd_{out2}$ in about 1 minute of computations on PC104 board. Other strategies different from the previously described mathematical models might be used, but the differential evolution algorithm has proven good and reliable results in most cases. Then, the calculated second outlet value $Cd_{out2}$ is used as significant value for the computation of at least one value of a parameter (D, $Cb_{in}$, K, K·t/V) indicative of the effectiveness of the extracorporeal blood treatment. In accordance with an aspect, if the parameter comprises is effective dialysance D, each computed value $D_k$ of the dialysance each respective variation is obtained using the formula:

$$D_k=(Q\text{dial}+\text{WLR})\cdot[1-(Cd_{out2}-Cd_{out1})/(Cd_{in2}-Cd_{in1})]$$

where:

$Cd_{out1}$ is the first outlet value taken by the characteristic in the spent dialysate line downstream of the secondary chamber in response to the change of characteristic $Cd_{in}$ in the preparation line to said first inlet value $Cd_{in1}$, $Cd_{out2}$ is the calculated second value (namely the significant value) which is representative of the value taken by the characteristic in the spent dialysate line downstream of the secondary chamber in response to the change of characteristic $Cd_{in}$ in the preparation line from said first inlet value $Cd_{in1}$ to said second inlet value $Cd_{in2}$, $Cd_{in1}$, $Cd_{in2}$ are first and second inlet values taken by the characteristic (Cd) in the preparation line upstream of the secondary chamber, Qdial is the fresh treatment liquid flow rate in the preparation line, WLR is the weight loss rate of a patient under treatment.

Figure 8:
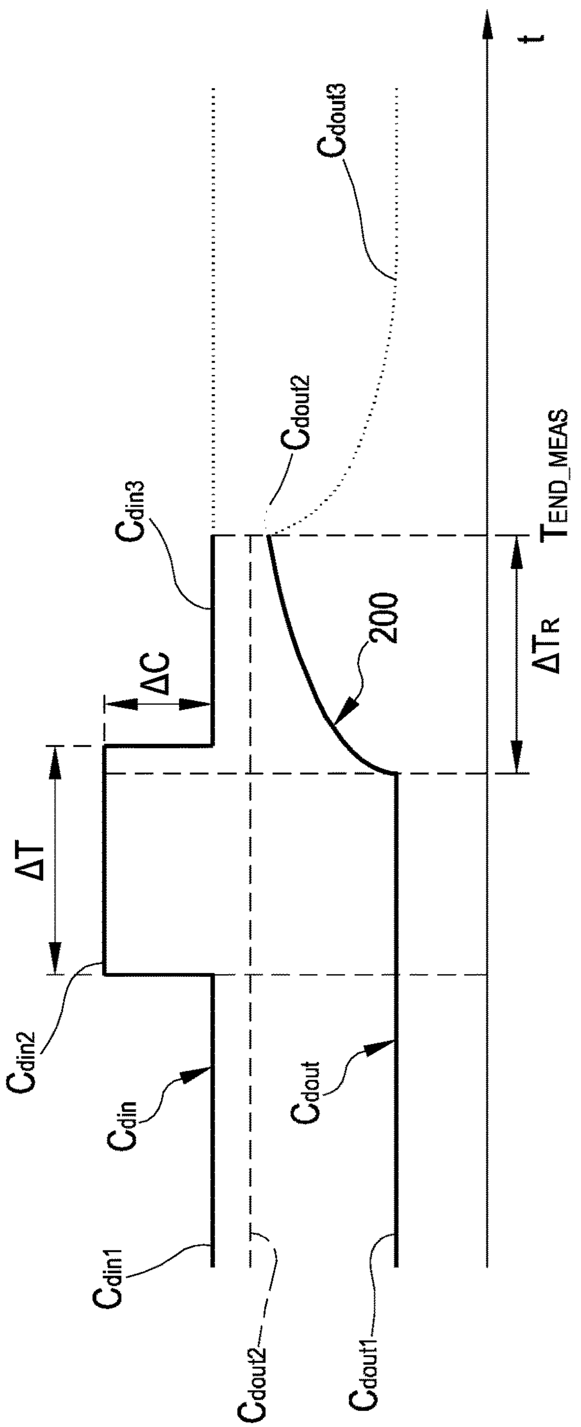

In FIGS. 7, 8 the upstream variation/perturbation is shorter and the value of the characteristic $Cd_{in}$ in the fresh treatment liquid is varied by imposing a change of the same from a first inlet value $Cd_{in1}$ to a second inlet value $Cd_{in2}$, which may optionally be kept constant for a prefixed time interval of e.g. 1 to 2 minutes, and then a further change to a third inlet value $Cd_{out3}$ thereby causing a corresponding change of the characteristic $Cd_{out}$ in spent liquid from a respective first outlet value $Cd_{out1}$ to a respective second outlet value $Cd_{out2}$ and then back to a third value $Cd_{out3}$ to define said timely delayed downstream variation of the characteristic $Cd_{out}$. In the example of FIGS. 7 and 8, $Cd_{in1}$ is equal or close to $Cd_{in3}$. In case a short variation/perturbation is used, the formula needed for the calculation of the effectiveness parameter requires more than simply the knowledge of one significant value such as $Cd_{out2}$. In the example of FIGS. 7 and 8, the reference portion of the downstream variation begins after the characteristic in the spent liquid changes from said first outlet value $Cd_{out}$ and lasts a period—for instance prefixed period $\Delta T_R$—during which the characteristic either continuously increases or decreases. During $\Delta T_R$ the characteristic $Cd_{out}$ may or may not reach the second outlet value $Cd_{out2}$. In accordance with an aspect, there is no need to wait until $Cd_{out}$ reaches $Cd_{out2}$ and returns to the baseline value $Cd_{out3}$. Instead, the second and third $Cd_{out2}$ and $Cd_{out3}$ or at least the third outlet value $Cd_{out3}$ of the characteristic $Cd_{out}$ are/is calculated by using as input to the characteristic mathematical model the values of characteristic $Cd_{in}$ in the fresh treatment liquid, or a mathematically calculated version of the characteristic $Cd_{in}$ in the fresh treatment liquid.

Once the values $Cd_{out1}$, $Cd_{out2}$, $Cd_{out3}$ have been calculated, the effectiveness parameter may be determined based on these calculated values and on one or more inlet values of the conductivity, e.g. $Cd_{in1}$, $Cd_{in2}$, $Cd_{in3}$.

For instance if dialysance is to be calculated, the following formula may be adopted:

$$D=(Q\text{dial}+\text{WLR})[1-(2\times Cd_{out1}-Cd_{out2}-Cd_{out3})/(2\times Cd_{in1}-Cd_{in2}-Cd_{in3})]$$

where:

$Cd_{out1}$ is the first outlet value taken by the characteristic in the spent dialysate line downstream of the secondary chamber in response to the change of characteristic $Cd_{in}$ in the preparation line to said first inlet value $Cd_{in1}$, $Cd_{out2}$ is the calculated second value (namely one of the significant values) which is representative of the value taken by the characteristic in the spent dialysate line downstream of the secondary chamber in response to the change of characteristic $Cd_{in}$ in the preparation line from said first inlet value $Cd_{in2}$ to said second inlet value $Cd_{in2}$, $Cd_{out3}$ is the calculated third value (namely one of the significant values) which is representative of the value taken by the characteristic in the spent dialysate line downstream of the secondary chamber in response to the change of characteristic $Cd_{in}$ in the preparation line from said second inlet value $Cd_{in2}$ to said third inlet value $Cd_{in3}$, $Cd_{in1}$, $Cd_{in2}$, $Cd_{in3}$ are first, second and third inlet values taken by the characteristic (Cd) in the preparation line upstream of the secondary chamber, Qdial is the fresh treatment liquid flow rate in the preparation line, WLR is the weight loss rate of a patient under treatment.

Figure 9:
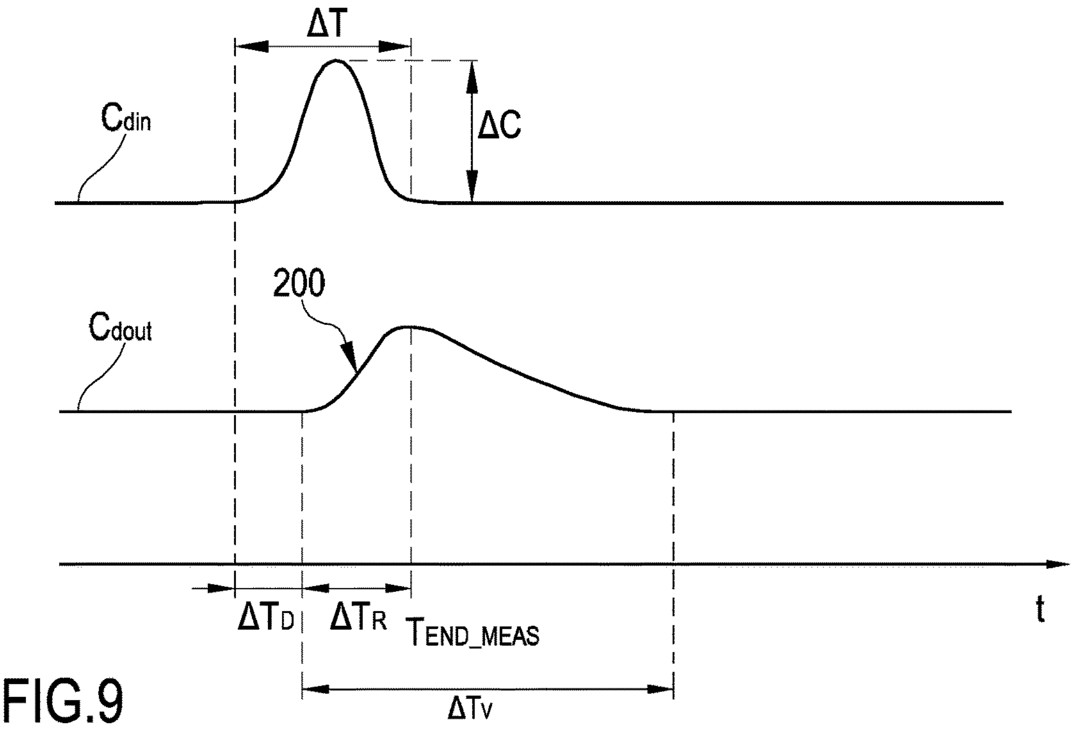
FIG. 9 shows a conductivity (or concentration) vs. time diagram in the fresh and in the spent dialysate line wherein the conductivity (or concentration) variation in the fresh dialysate line is in the form of pulse.

According to a further embodiment, see FIG. 9, varying the value of the characteristic $Cd_{in}$ in the fresh treatment liquid comprises imposing an upstream variation/perturbation, which may be in the shape of a sinusoid or of a short peak, in the characteristic of the fresh treatment liquid thereby causing a corresponding downstream variation/perturbation of the characteristic $Cd_{out}$ in spent liquid. The reference portion of said downstream variation/perturbation begins after the characteristic in the spent liquid changes from said first outlet value $Cd_{out1}$ and lasts a prefixed period shorter than a fraction, e.g. 60% or even 50%, of the duration of the entire downstream variation/perturbation. The control unit 10 determines in this case a plurality, e.g. 10 or more, of significant values of the characteristic $Cd_{out}$, describing a remaining portion of the downstream variation/perturbation consecutive to said reference portion, by using as input to the mathematical model the values of characteristic $Cd_{in}$ in the fresh treatment liquid, or a mathematically calculated version of the characteristic $Cd_{in}$ in the fresh treatment liquid, thereby obtaining a calculated downstream variation/perturbation from said extrapolated significant values.

Then, using e.g. the formulas described in EP 0920877, the control unit computes at least one value of a parameter (D, $Cb_{in}$, K, K·t/V) indicative of the effectiveness of the extracorporeal blood treatment by comparing the calculated downstream variation/perturbation and the upstream variation/perturbation.

In accordance with a further aspect of the invention, the control unit 10 may also be configured to determine the baseline of the downstream curve representative of the values $Cd_{out(t)}$ taken over time by said characteristic in the spent dialysate line downstream of the secondary chamber. The baseline of the downstream curve $Cd_{out(t)}$ may be determined using measured values of the characteristic $Cd_{out}$ in the spent liquid or using a calculated curve representative of the downstream variation which has been previously determined using the characteristic mathematical model. In this second option only measured values of the characteristic $Cd_{out}$ in the spent liquid during said reference portion are used for the determination of the free parameters to identify the characteristic mathematical model; then using said identified characteristic mathematical model, a downstream curve $Cd_{out(t)}$ representative of the values taken by the characteristic $Cd_{out}$ in the spent liquid is mathematically determined and the baseline thereof identified.

Figure 10:
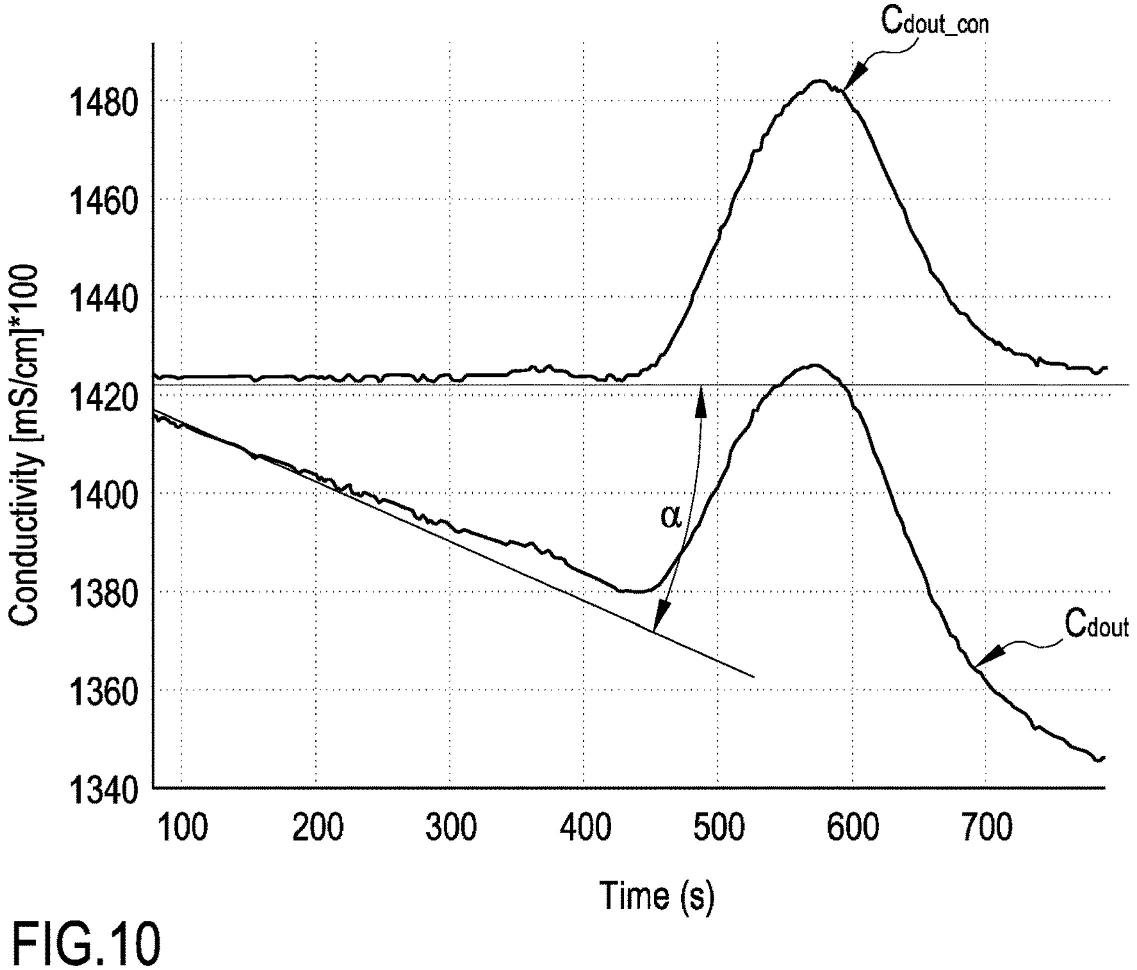
FIG. 10 is a diagram showing the outlet conductivity (or concentration) vs. time and schematically illustrating an angular correction of the conductivity (or concentration) baseline.

The control unit may be configured to determine an angular deviation a between the baseline of the downstream curve $Cd_{out(t)}$ with respect to the prescription baseline $Cd_{set}$, and to compensate for said angular deviation by angularly rotating the downstream curve to obtain a corrected downstream curve $Cd_{out\text{-}correct(t)}$, as shown in a the enlarged representation of FIG. 10.

According to a yet further aspect, the control unit 10 is configured to remove undesired noise from the characteristic $Cd_{out}$. In accordance with an aspect, the control unit may receive measured values of the characteristic $Cd_{out}$ in the spent liquid during said reference portion, estimate the free parameters of the parametric mathematical model to identify the characteristic mathematical model, determine a downstream curve $Cd_{out(t)}$ representative of the values taken by the characteristic $Cd_{out}$ in the spent liquid using said identified characteristic mathematical model, analyze a frequency spectrum of the downstream curve $Cd_{out(t)}$, filter out harmonics of said frequency spectrum of the downstream curve $Cd_{out(t)}$ lying at frequencies higher than a prefixed threshold to eliminate noise and undesired perturbations possibly present in the downstream curve and obtain a corrected downstream curve $Cd_{out\text{-}correct(t)}$.

Although the above description referred to one single parametric mathematical model, the control unit 10 may further be configured for storing a plurality of mathematical models each of which puts into relation the characteristic ($Cd_{in}$) in the fresh treatment liquid with the characteristic ($Cd_{out}$) in the spent liquid. In this case the control unit may be configured for selecting the mathematical model to be used for computing the at least one significant value of said downstream variation based on certain factors such as for instance: the shape of the upstream variation (one mathematical model may be better suited for a long step variation/perturbation while another model may more properly operate for a short sinusoidal change), the type of blood treatment unit used by the apparatus, whether or not particular hydraulic components are present in the circuit section between sensor 109 and sensor 109*a*.

Figure 11:
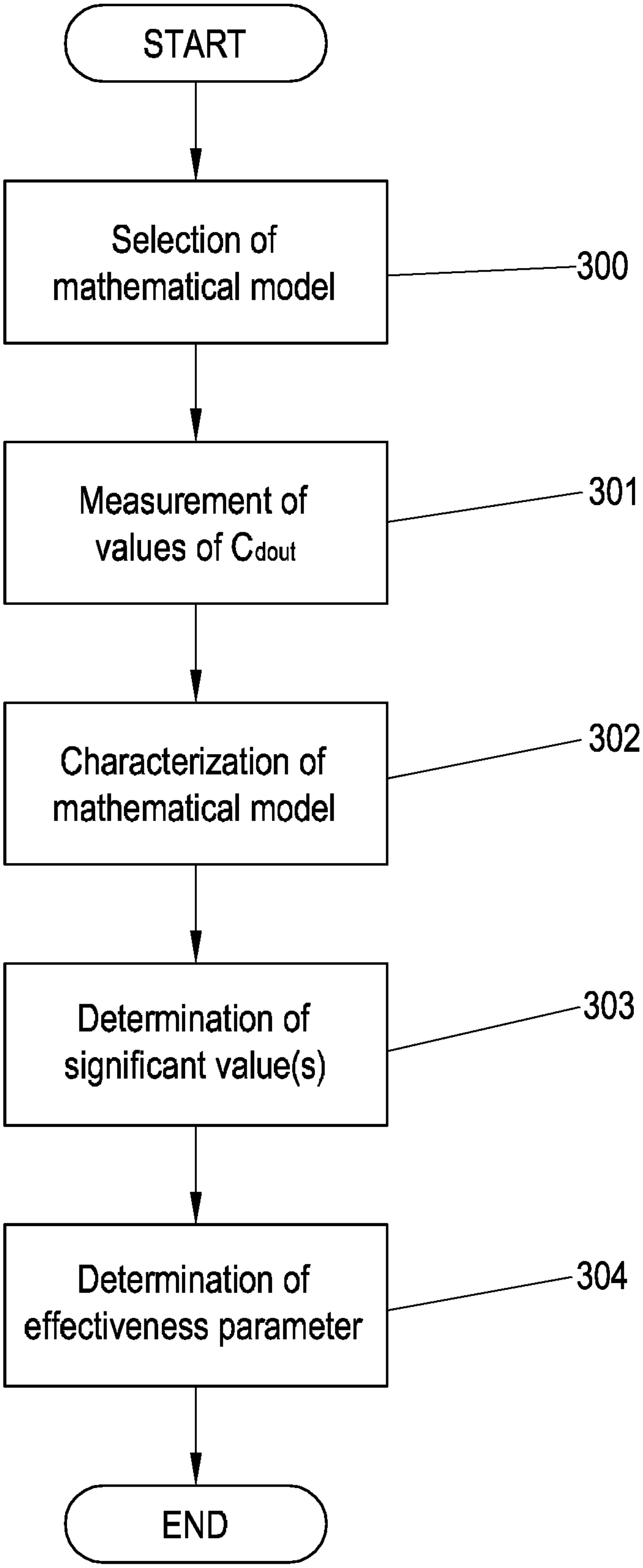
FIG. 11 is a schematic flowchart of a method according to one aspect of the invention.

Aspects of the invention are also disclosed in FIG. 11, which shows a flowchart exemplifying a method for determining an effectiveness parameter. The method may be executed by the control unit 10 of any one of the apparatuses disclosed herein above or claimed in the appended claims.

The method comprises the following steps.

step 300: selection of the mathematical model;

step 301: measurement of values of conductivity, or concentration, $Cd_{out}$ in the spent dialysate corresponding to a variation respectively in the conductivity, or in the concentration of at least one substance, $Cd_{in}$ made on the fresh dialysis liquid flowing upstream the blood treatment unit (step 301); the measures are taken during the reference time $\Delta T_R$ which is sensibly shorter than the duration of the downstream variation, as already explained herein above;

step 302: characterization of mathematical model using the measured value(s) of $Cd_{out}$ taken during the reference time $\Delta T_R$ and identification of a single mathematical model;

step 303: determination, using the mathematical model, of significant value(s) necessary for the calculation of the effectiveness parameter; the significant values may be one or more calculated conductivity or concentration values of the downstream variation at instants following the reference period (such as $Cd_{out2}$ or $Cd_{out2}$ and $Cd_{out3}$);

step 304: determination of effectiveness parameter using the calculated significant value or values.

The calculation of the effectiveness parameter may be made using any one of the formulas described above.

Example 1

Here below an example is described, with reference to FIGS. 12-15, showing use of a one-zero and three-pole mathematical model to mathematically calculate the entire downstream variation; it is relevant noticing that to characterize the model, only measured values relative to a reference portion of the downstream variation having relatively short duration compared to the duration of the entire downstream variation are used. The Example provided adopts an exemplifying mathematical model and makes reference to a step variation/perturbation imposed in the liquid flowing upstream the blood treatment unit. Of course other mathematical models may be adopted and the upstream variation/perturbation may be different from a step-shaped variation/perturbation.

Furthermore, the example makes reference to conductivity variations and corresponding measures: of course the same procedure may be adopted using variations, and corresponding measures, in the concentration of at least one substance in the dialysis liquid.

Figure 12:
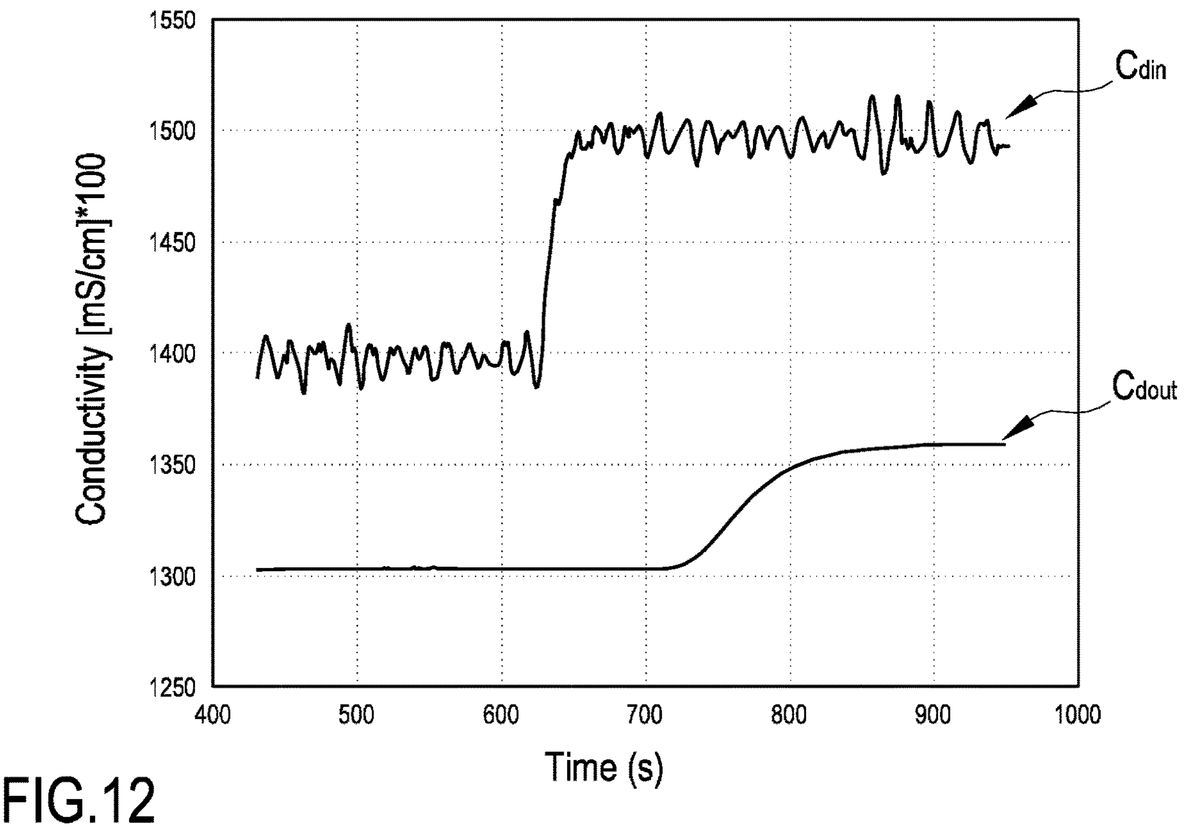
FIG. 12 shows a conductivity (mS·100/cm) vs. time (seconds) diagram showing the real measured conductivity profile in the fresh and in the spent dialysate line in the case of a step conductivity variation in the fresh dialysate of 1 mS/cm.
Figure 13:
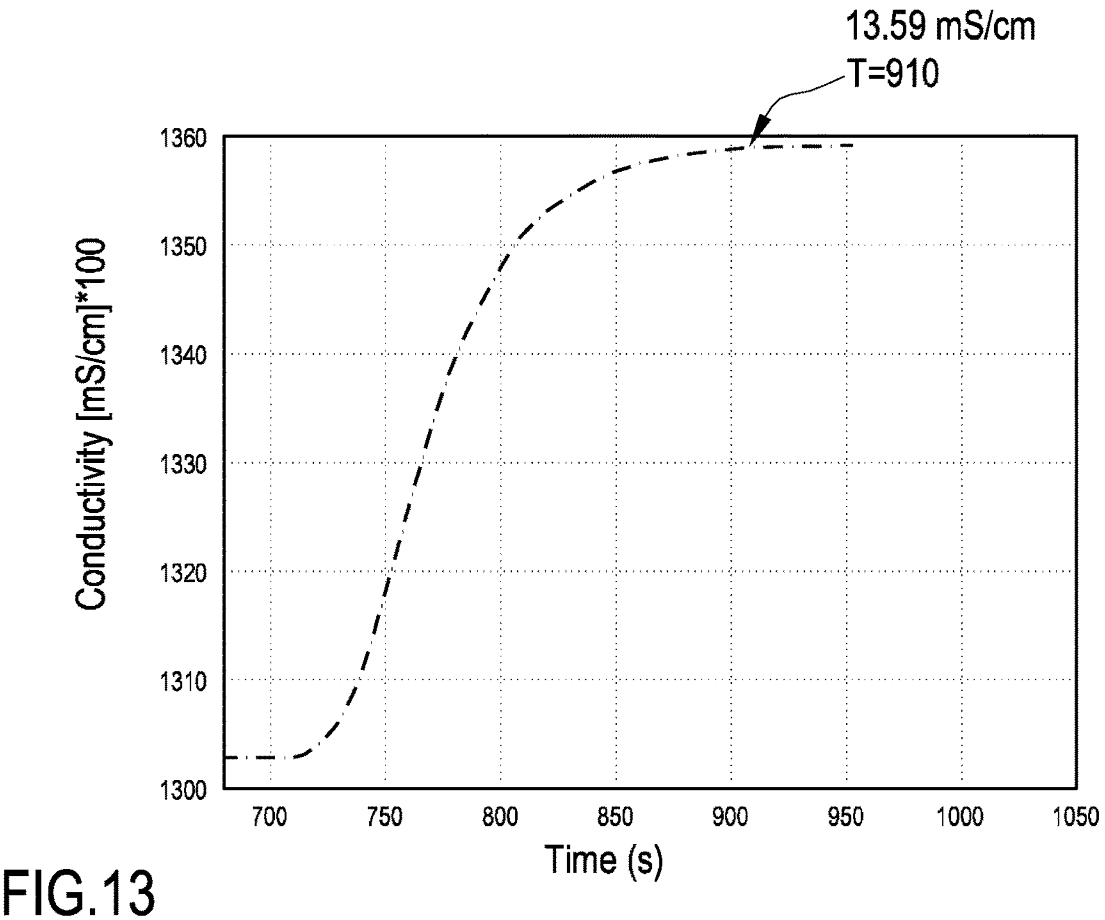
FIG. 13 is an enlarged view of the measured outlet conductivity profile of FIG. 12.
Figure 14:
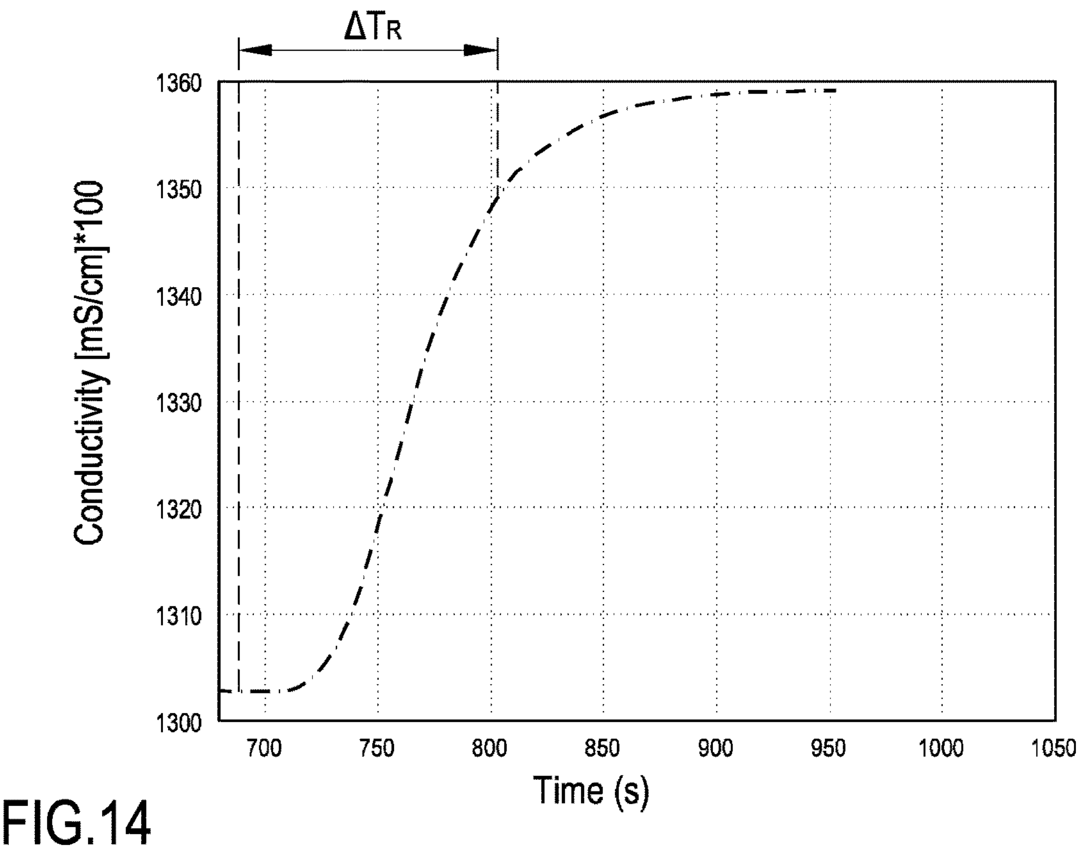
FIG. 14 is an enlarged view of the measured outlet conductivity profile of FIG. 12 where the reference time $\Delta T_R$ is identified.

Referring now to the diagram of FIG. 12, two curves are represented: a first curve represents the inlet conductivity $Cd_{in}$ and shows a step-shaped conductivity variation (1 mS/cm) that has been imposed to the conductivity of the dialysis liquid flowing upstream the blood treatment unit, while a second curve (below the first curve) represents the downstream conductivity $Cd_{out}$ and shows the corresponding variation in the conductivity of the spent dialysis liquid as a consequence of the step-shaped variation/perturbation on the upstream conductivity $Cd_{in}$. FIG. 13 is an enlarged view of FIG. 12 and focuses on the outlet conductivity: notice that the curve in FIG. 13 is obtained measuring the outlet conductivity values from time 700 s to time 950 s (i.e. 250 seconds). FIG. 13 shows the value of the outlet conductivity $Cd_{out2}$ at time 910 which is regarded as the significant value of interest, necessary for the calculation of e.g. dialysance when using formula:

$$D_k=(Q\text{dial}+\text{WLR})\cdot[1-(Cd_{out2}-Cd_{out1})/(Cd_{in2}-Cd_{in1})]$$

According to one aspect of the invention, instead of measuring the conductivity values until time 950 s, measures are taken only during reference portion $\Delta T_R$ (please refer to FIG. 14) i.e. for the 100 seconds only Then, using the following a one-zero and three-pole model:

$$H(z)=\frac{a_0}{1-b_1z^{-1}-b_2z^{-2}-b_3z^{-3}}$$

The following parameters are estimated using the measured values of $Cd_{out}$ during reference portion $\Delta T_R$:

a0=0.004209932871 b1=−2.905495405197 b2=2.815777778625 b3=−0.910210132599 giving $$H(z)=\frac{0.004209932871}{1-2.905495405197z^{-1}+2815777778625z^{-2}-0.910210132599z^{-3}}$$

Figure 15:
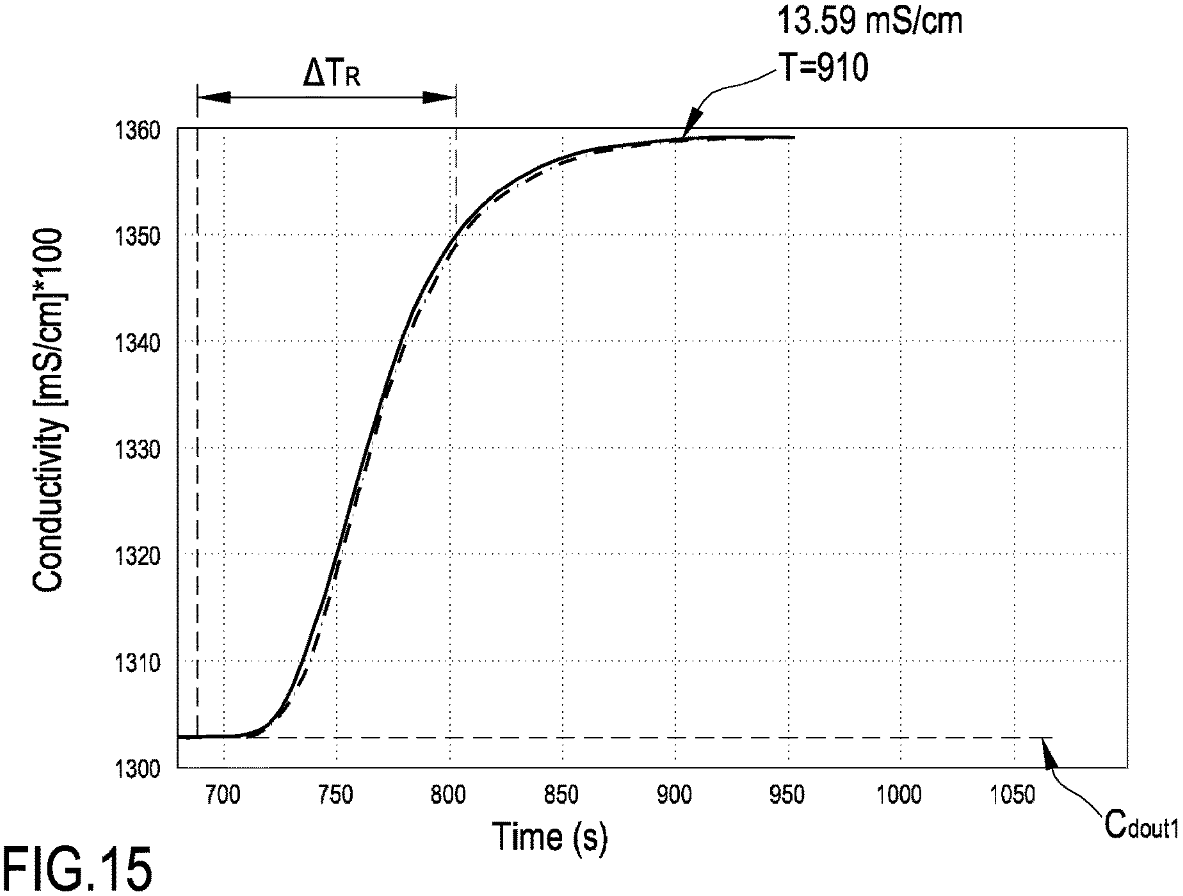
FIG. 15 is an enlarged view of the measured outlet conductivity profile of FIG. 12 (dotted line) and of the calculated curve representing the outlet conductivity as determined using a mathematical model according to aspects of the invention.

By feeding an idealized unit step (i.e. a calculated step) of appropriate length (e.g. 200 to 300 s) to this model and by suitably adding the baseline value $Cd_{out1}$ to the model output, we get a signal as shown in FIG. 15 (continuous line represents model output, while dotted line schematically represents measured $Cd_{out}$), which closely approximates the behavior of the system in a time interval following the reference portion.

The following table shows the measured versus computed values of $Cd_{out}$ in the neighborhood of time n=910 where the good match between measured and computed values can be seen.

| Time | $Cd_{out}$ model (mS · 100/cm) | $Cd_{out}$ measured (mS · 100/cm) |
|---|---|---|
| 905 | 1358.567173 | 1359 |
| 906 | 1358.586262 | 1359 |
| 907 | 1358.604656 | 1359 |
| 908 | 1358.622398 | 1359 |
| 909 | 1358.639698 | 1359 |
| 910 | 1358.656872 | 1359 |
| 911 | 1358.674126 | 1359 |
| 912 | 1358.691517 | 1359 |
| 913 | 1358.709053 | 1359 |
| 914 | 1358.726700 | 1359 |
| 915 | 1358.744549 | 1359 |

The calculated significant value $Cd_{out2}$ at time 910 is 13.59 mS/cm is very close to the corresponding measured value (13,58656872 mS/cm). Thus, the dialysance calculation using the above formula and relying on the calculated value $Cd_{out2}$ of 13.59 mS/cm will provide exactly the same result as when using a measured valued for $Cd_{out2}$, while requiring actual measurements only during $\Delta T_R$.

Upstream Variation

According to one aspect of the invention, the control unit is configured to compute the extent (duration over time $\Delta T$ and/or the amplitude $\Delta C_{in}$) of the mentioned upstream variation of the value of the characteristic $Cd_{in}$ in the fresh treatment liquid with respect to said prescription baseline $Cd_{set}$ as a function of the working conditions of the apparatus and in particular of the flow rate Qdial of the fresh treatment liquid in the preparation line 19 and/or of another parameter correlated to the flow rate Qdial. Indeed, a parameter proportional to the flow rate Qdial or a known function of the flow rate Qdial may alternatively be used as flow rate Qdial. Extent of the upstream variation is computed in order to tune and optimize said upstream variation as a function of the effective flow rate Qdial and to minimize the effects of undesired modifications of the characteristic of the dialysis liquid on patients. In this way, the best duration over time $\Delta T$ and/or the best amplitude $\Delta C_{in}$ are/is set at each flow rate Qdial of the fresh treatment liquid during treatment, meaning that the best compromise "precision vs treatment interruption" is ensured and unnecessary machine time to determine the effectiveness parameter is avoided.

Note that this aspect related to the optimization of the upstream variation may also be independent from the implementation of the parametric mathematical model detailed above. Indeed, the values correlated to the downstream variation may also be all measured and/or calculated in some other way and used to compute said at least one value of a parameter indicative of the effectiveness of the extracorporeal blood treatment without using the parametric mathematical model.

Figure 17:
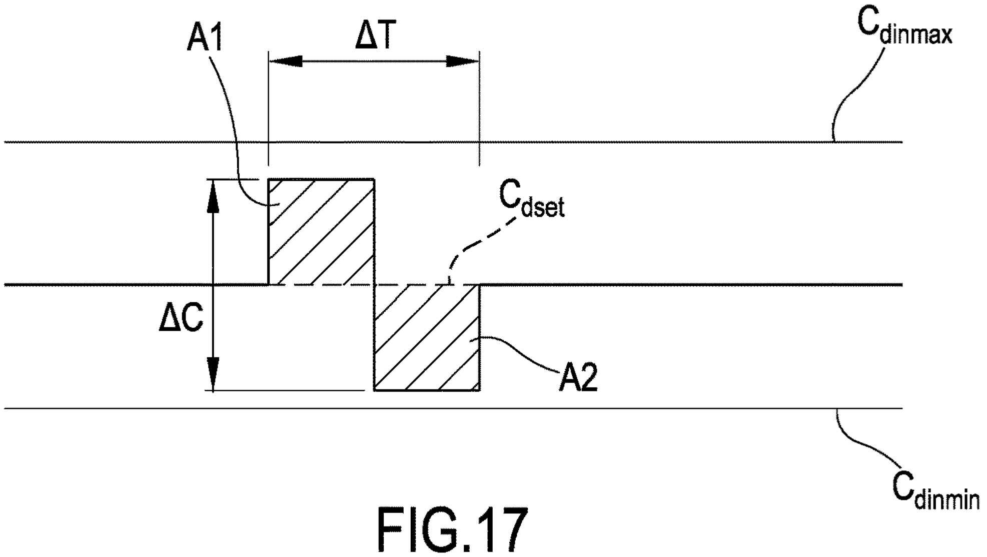
FIGS. 17, 18 and 19 show a conductivity (or concentration) vs. time diagrams showing the conductivity (or concentration) profile in the fresh dialysate line, according other aspects of the invention.
Figure 18:
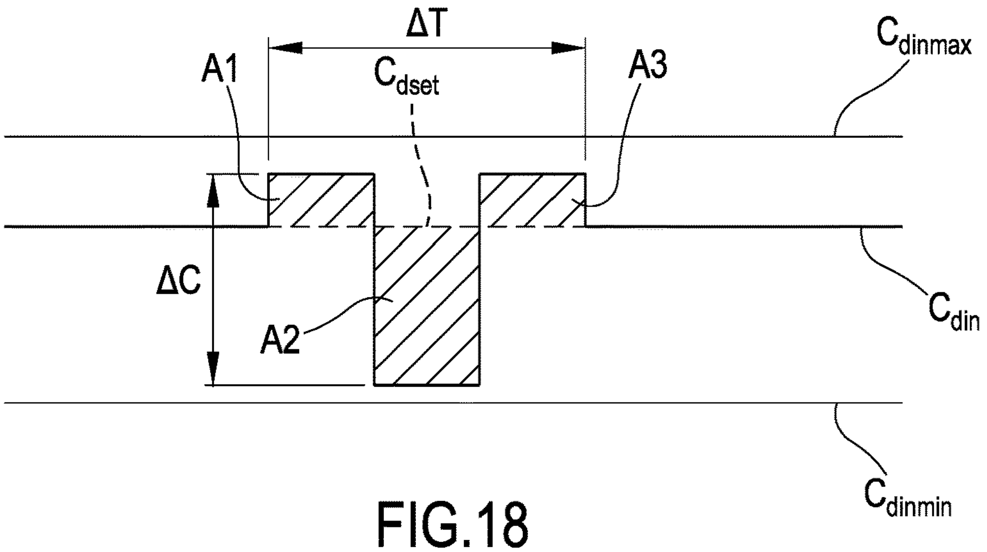

As schematically shown in FIGS. 4, 7, 8 and 9, the upstream variation may be in the shape of a rectangle or square or of a bell or a peak or a sinusoid. Said upstream variation has an amplitude $\Delta C_{in}$ and a duration over time $\Delta T$. The duration over time $\Delta T$ is a time frame during which the characteristic $Cd_{in}$ is different from the prescription baseline $Cd_{set}$. In FIGS. 4, 7, 8 and 9, the upstream variation is all above (higher than) the prescription baseline $Cd_{set}$ but the upstream variation may also be all below (lower than) the prescription baseline $Cd_{set}$, like in FIG. 19. The upstream variation is a difference between a maximum or a minimum of the upstream variation and the prescription baseline $Cd_{set}$. In FIGS. 17 and 18, the upstream variation comprises two or three consecutive parts placed one after the other and extending above the prescription baseline $Cd_{set}$ and below the prescription baseline $Cd_{set}$. The part/s above the prescription baseline $Cd_{set}$ are arranged alternately with the part/s below the prescription baseline $Cd_{set}$ such that the caused upstream variation of the value of the characteristic in the fresh treatment liquid decreases and increases with respect to the prescription baseline $Cd_{set}$ for such characteristic. The amplitude $\Delta C_{in}$ is a difference between a maximum and a minimum of the upstream variation. The duration over time $\Delta T$ is a sum of partial durations over time of the part/s above the prescription baseline $Cd_{set}$ and the part/s below the prescription baseline $Cd_{set}$.

It is feasible to reduce the duration over time $\Delta T$ and/or the amplitude $\Delta C_{in}$ as a function of increase of the flow rate Qdial of the fresh treatment liquid. In other words, the amplitude $\Delta C_{in}$ and/or the duration over time $\Delta T$ are/is increased if the flow rate Qdial of the fresh treatment liquid is reduced and the amplitude $\Delta C_{in}$ and/or the duration over time $\Delta T$ are/is reduced if the flow rate Qdial of the fresh treatment liquid is increased.

Figure 16:
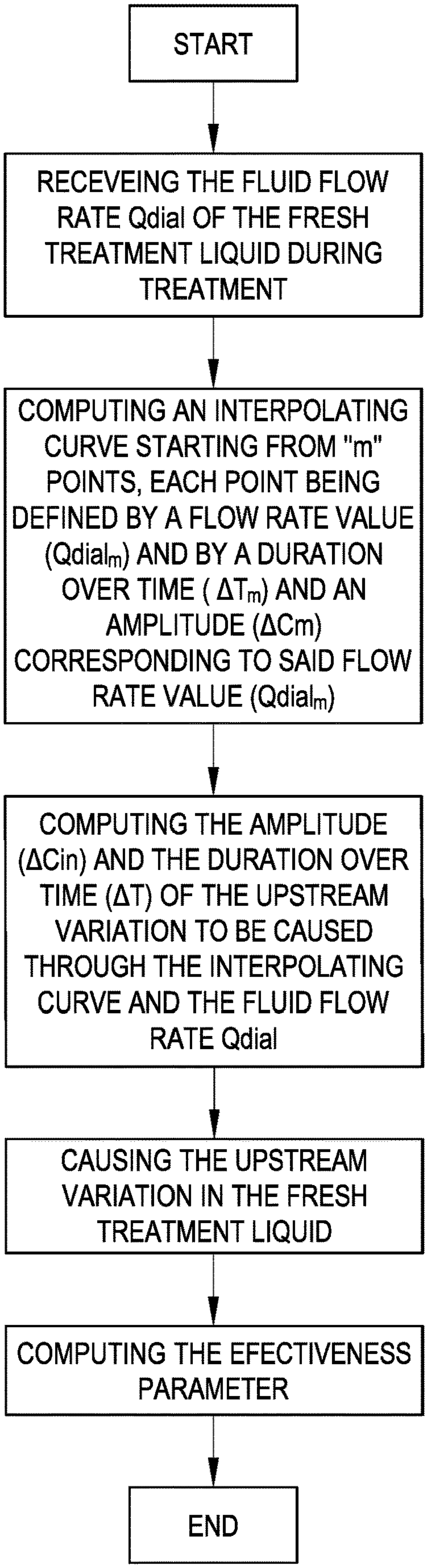
FIG. 16 is another schematic flowchart of a method according to one aspect of the invention.

The computed duration over time may be between 50 s and 200 s, optionally between 90 s and 150 s. The characteristic $Cd_{in}$ may be the conductivity in the fresh treatment liquid and the computed amplitude of said conductivity may be between 0.4 mS/cm and 1.1 mS/cm, optionally between 0.5 mS/cm and 1 mS/cm. The flow rate Qdial of the fresh treatment liquid during treatment being may be between 250 ml/min and 850 ml/min, optionally between 300 ml/min and 800 ml/min. According to some embodiments, the duration over time $\Delta T$ and/or the amplitude $\Delta C_{in}$ are/is inversely proportional with respect to the flow rate of the fresh treatment liquid. According to some embodiments, the duration over time $\Delta T$ and/or the amplitude $\Delta C_{in}$ are/is computed through an interpolating curve (a method of the invention is illustrated in FIG. 16).

Duration over time $\Delta T$ may be computed using the following interpolating curve.

$$\Delta T=((\Delta T_{min}-\Delta T_{max})/(Qdial_{max}-Qdial_{min}))*(Qdial-Qdial_{max})+\Delta T_{min} \quad \text{i)}$$

where:

Qdial is the flow rate of the fresh treatment liquid in the preparation line, e.g. measured by the flow sensor 110 during treatment or set as working parameter;

$Qdial_{max}$ is a maximum flow rate of the apparatus (e.g between 750 ml/min and 850 ml/min);

$\Delta T_{min}$ is a minimum duration over time corresponding to the maximum flow rate of the apparatus (e.g between 80 s and 100 s);

$Qdial_{min}$ is a minimum flow rate of the apparatus (e.g between 250 ml/min and 350 ml/min);

$\Delta T_{max}$ is a maximum duration over time corresponding to the minimum flow rate of the apparatus (e.g between 140 s and 160 s).

Said maximum flow rate $Qdial_{max}$, said a minimum duration over time $\Delta T_{min}$, said a minimum flow rate $Qdial_{min}$, said maximum duration over time $\Delta T_{max}$ are values pre-stored in the memory of the control unit 10 as factory settings or transferred to said memory via user interface 12 or via other input means, such as a data reader, or it may be remotely transmitted from a remote source.

Amplitude $\Delta C_{in}$ may be computed using the following interpolating curve.

$$\Delta C_{in}=((\Delta C_{min}-\Delta C_{max})/(Qdial_{max}-Qdial_{min}))*(Qdial-Qdial_{max})+\Delta C_{min} \quad \text{ii)}$$

where:

Qdial is the flow rate of the fresh treatment liquid in the preparation line;

$Qdial_{max}$ is the maximum flow rate of the apparatus;

$\Delta C_{in}$ is a minimum amplitude corresponding to the maximum flow rate of the apparatus (e.g a conductivity amplitude between 0.4 mS/cm and 0.6 mS/cm);

$Qdial_{min}$ is the minimum flow rate of the apparatus;

$\Delta C_{max}$ is a maximum amplitude corresponding to the minimum flow rate of the apparatus (e.g a conductivity amplitude between 0.9 mS/cm and 1.1 mS/cm).

Said maximum flow rate $Qdial_{max}$, said a minimum amplitude $\Delta C_{min}$, said a minimum flow rate $Qdial_{min}$, said maximum amplitude $\Delta C_{max}$ are values pre-stored in the memory of the control unit 10 as factory settings or transferred to said memory via user interface 12 or via other input means, such as a data reader, or it may be remotely transmitted from a remote source.

The interpolating curves of the embodiments mentioned above are each computed starting only from two flow rates $Qdial_{max}$ and $Qdial_{min}$ (and corresponding $\Delta C_{max}$, $\Delta C_{min}$ or $\Delta T_{max}$, $\Delta T_{min}$). In other embodiments, the interpolating curves may be computed starting from "m" points wherein "m" is equal to or greater than two. Each of the "m" points is defined by a flow rate value $Qdial_m$ of the fresh treatment liquid and by a duration over time $\Delta T_m$ and/or by an amplitude $\Delta C_m$ of the characteristic $Cd_{in}$ corresponding to said flow rate value $Qdial_m$. For instance, the interpolating curve is computed starting from the above mentioned maximum flow rate $Qdial_{max}$ and a minimum flow rate $Qdial_{min}$ and also from a third point, for instance a mid flow rate $Qdial_{mid}$ of the apparatus comprised between the maximum flow rate $Qdial_{max}$ and the minimum flow rate $Qdial_{min}$ and corresponding to a mid duration over time $\Delta T_{mid}$ or to a mid amplitude $\Delta C_{mid}$.

Example 2

Here below an example is described.

The minimum flow rate of the apparatus $Qdial_{min}$ is 300 ml/min.

The maximum duration over time $\Delta T_{max}$ corresponding to the minimum flow rate $Qdial_{min}$ of the apparatus is 150 s.

The maximum flow rate of the apparatus $Qdial_{max}$ is 800 ml/min.

The minimum duration over time $\Delta T_{min}$ corresponding to the maximum flow rate $Qdial_{min}$ of the apparatus is 90 s.

The maximum amplitude of conductivity $\Delta C_{max}$ corresponding to the minimum flow rate $Qdial_{min}$ of the apparatus is 1 mS/cm.

The minimum amplitude of conductivity $\Delta C_{min}$ corresponding to the maximum flow rate $Qdial_{max}$ of the apparatus is 0.5 mS/cm.

The flow rate Qdial of the fresh treatment liquid in the preparation line during treatment is 500 ml/min. The duration over time ΔT of the upstream variation is computed using interpolating curve i):

$$\Delta T=((\Delta T_{min}-\Delta T_{max})/(Qdial_{max}-Qdial_{min}))*(Qdial-Qdial_{max})+\Delta T_{min}=((90-150)/(800-300))*(500-800)+90=126\text{ s}$$

The amplitude of the upstream variation of conductivity is computed using interpolating curve ii):

$$\Delta C_{in}=((\Delta C_{min}-\Delta C_{max})/(Qdial_{max}-Qdial_{min}))*(Qdial-Qdial_{max})+\Delta C_{min}=((0.5-1)/(800-300))*(500-800)+0.5=0.8\text{ mS/cm}$$

According to other embodiments, the amplitude $\Delta C_{in}$ and/or the duration over time ΔT are/is selected among "n" fixed amplitudes $\Delta C_1$, $\Delta C_n$ and/or fixed durations over time $\Delta T_1$, $\Delta T_n$ and each corresponding to a range, among "n" ranges ΔQdial1, $\Delta Qdial_n$ of the flow rate, in which the flow rate Qdial of the treatment falls. The plurality of fixed amplitudes $\Delta C_1$, $\Delta C_n$ and/or fixed durations over time $\Delta T_1$, $\Delta T_n$ and the "n" ranges ΔQdial1, $\Delta Qdial_n$ are stored in the memory of the control unit 10 as factory settings or transferred to said memory via user interface 12 or via other input means, such as a data reader, or it may be remotely transmitted from a remote source. The flow rate Qdial of the treatment may be measured through the flow sensor 110 or it is a or pre-set as working parameter of the treatment.

For instance, the control unit 10 receives "n" fixed durations over time $\Delta T_1$, $\Delta T_n$ (e.g. a first, second and third duration over time, respectively of 150 s, 120 s, 90 s) and "n" ranges ΔQdial1, $\Delta Qdial_n$ of the flow rate of the fresh treatment liquid (e.g. a first, second and third ranges of flow rate, respectively between 300-350/400 ml/min, 400-600/650 ml/min, 650-800 ml/min), wherein each of the "n" ranges is allocated to/combined with a fixed duration over time of "n" of said fixed durations over time $\Delta T_1$, $\Delta T_n$. Then the control unit 10 receives the flow rate Qdial of the treatment and computes the duration over time ΔT of the upstream variation to be generated by comparing the received flow rate Qdial with the "n" ranges ΔQdial1, $\Delta Qdial_n$ and by selecting the fixed duration over time corresponding to the range of said "n" ranges which the flow rate Qdial falls in.

The control unit 10 further receives "n" fixed amplitudes $\Delta C_1$, $\Delta C_n$ (e.g. a first, second and third amplitude of conductivity, respectively of 0.5 mS/cm, 0.7 mS/cm, 1 mS/cm) and the "n" ranges ΔQdial1, $\Delta Qdial_n$ of the flow rate of the fresh treatment liquid, wherein each of the "n" ranges is allocated to/combined with a fixed amplitude of "n" fixed amplitudes $\Delta C_1$, $\Delta C_n$. Then the control unit 10 receives the flow rate Qdial of the treatment and computes the amplitude $\Delta C_{in}$ of the upstream variation to be generated by comparing the received flow rate Qdial with the "n" ranges ΔQdial1, $\Delta Qdial_n$ and by selecting the fixed amplitude $\Delta C_{in}$ corresponding to the range of said "n" ranges which the flow rate Qdial falls in.

According to one aspect of the invention, the control unit 10 is configured to compute and generate the upstream variation so that said upstream variation is lower than a maximum allowed value $Cd_{in\ max}$ (e.g. 1.5 mS/cm) of the characteristic $Cd_{in}$ in the fresh treatment liquid and higher than a minimum allowed value $Cd_{in\ min}$ (e.g. 0.1 mS/cm) of the characteristic $Cd_{in}$ in the fresh treatment liquid.

Figure 19:
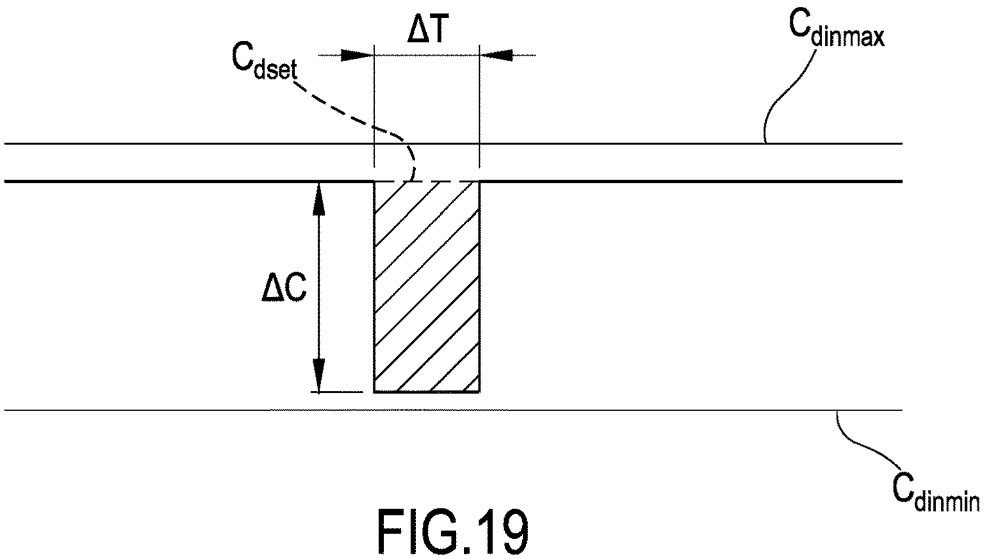

If the prescription baseline $Cd_{set}$ is close to the minimum allowed value $Cd_{in\ min}$, the upstream variation is computed and generated to be all above said prescription baseline $Cd_{set}$, as shown in FIG. 4. If the prescription baseline $Cd_{set}$ is close to the maximum allowed value $Cd_{in\ max}$, the upstream variation is computed and generated to be all below said prescription baseline $Cd_{set}$, as shown in FIG. 19.

According to one aspect of the invention, the control unit 10 is configured to compute and generate the upstream variation so that said upstream variation comprises at least two consecutive parts placed one after the other, one part extending above the prescription baseline $Cd_{set}$ and the other part extending below the prescription baseline $Cd_{set}$ (as mentioned above and shown in FIGS. 17 and 18), and such that a total area of the part or parts of the upstream variation above the prescription baseline $Cd_{set}$ is equal to or substantially equal to a total area of the part or parts of the upstream variation below the prescription baseline $Cd_{set}$. This would ensure that a total sodium balance with the patient will be neutral or substantially neutral.

FIG. 17 shows an upstream variation comprising a first part above the prescription baseline $Cd_{set}$ and delimiting a first area Aland a second part extending below the prescription baseline $Cd_{set}$ and delimiting a second area A2 equal to A1. FIG. 18 shows an upstream variation comprising a first part above the prescription baseline $Cd_{set}$ and delimiting a first area A1, a second part extending below the prescription baseline $Cd_{set}$ and delimiting a second area A2 and a third part extending above the prescription baseline $Cd_{set}$ and delimiting a third area A3, wherein A2 is equal to the sum of A1 and A3. If the prescription baseline $Cd_{set}$ is close to the the maxium allowed value $Cd_{in\ max}$ and also to the minimum allowed value $Cd_{in\ min}$ (with respect to an amplitude of the upstream variation for a treatment), the upstream variation provided with parts above and below the prescription baseline $Cd_{set}$ allows to keep said upstream variation between the maxium allowed value $Cd_{in\ max}$ and the minimum allowed value $Cd_{in\ min}$. For instance, the control unit 10 computes the duration over time $\Delta T$ and the amplitude $\Delta C_{in}$, then compares the upstream variation of the characteristic $Cd_{in}$ with the minimum allowed value $Cd_{in}$ min and with the maximum allowed value $Cd_{in\ max}$ and, if the upstream variation exceeds the said minimum and maximum allowed values $Cd_{in\ min}$, $Cd_{in\ max}$, adjusts the position of the upstream variation with respect to the prescription baseline $Cd_{set}$ and/or computes the number of consecutive parts, in order to maintain the upstream variation between the maxium allowed value $Cd_{in\ max}$ and the minimum allowed value $Cd_{in\ min}$ and/or such that the total area of the part or parts of the upstream variation above the prescription baseline $Cd_{set}$ is equal to or substantially equal to the total area of the part or parts of the upstream variation below the prescription baseline $Cd_{set}$.

Control Unit

As already indicated the apparatus according to the invention makes use of at least one control unit 10. This control unit 10 may comprise a digital processor (CPU) with memory (or memories), an analogical type circuit, or a combination of one or more digital processing units with one or more analogical processing circuits. In the present description and in the claims it is indicated that the control unit 10 is "configured" or "programmed" to execute certain steps: this may be achieved in practice by any means which allow configuring or programming the control unit 10. For instance, in case of a control unit 10 comprising one or more CPUs, one or more programs are stored in an appropriate memory: the program or programs containing instructions which, when executed by the control unit 10, cause the control unit 10 to execute the steps described and/or claimed in connection with the control unit 10. Alternatively, if the control unit 10 is of an analogical type, then the circuitry of the control unit 10 is designed to include circuitry configured, in use, to process electric signals such as to execute the control unit 10 steps herein disclosed.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the scope of the appended claims.

The invention claimed is:

1. An apparatus for an extracorporeal treatment of blood comprising:

a blood treatment unit having a primary chamber and a secondary chamber separated by a semi-permeable membrane;

a preparation line having one end connected to an inlet of the secondary chamber of the blood treatment unit and configured to convey fresh treatment liquid to the secondary chamber, the fresh treatment liquid presenting a characteristic selected from a group consisting of:

a conductivity in the fresh treatment liquid, and a concentration of at least one substance in the fresh treatment liquid;

a spent dialysate line having one end connected to an outlet of said secondary chamber and configured to remove spent liquid from the secondary chamber, the spent liquid presenting a characteristic selected from a group consisting of:

a conductivity in the spent liquid, and a concentration of at least one substance in the spent liquid; and a control unit configured to command execution of a task for determining a parameter indicative of an effectiveness of the extracorporeal treatment of blood, said task comprising the following steps:

receiving at least one prescription baseline for the characteristic in the fresh treatment liquid, receiving a minimum duration over time corresponding to a maximum flow rate of the apparatus, receiving a maximum duration over time corresponding to a minimum flow rate of the apparatus, receiving a flow rate, or a parameter correlated to the flow rate, of the fresh treatment liquid in the preparation line, causing the fresh treatment liquid to flow in the preparation line to the secondary chamber with the characteristic being at said at least one prescription baseline, causing the spent liquid to flow out of the secondary chamber into the spent dialysate line, computing a duration over time interpolating curve based on the minimum duration over time, the maximum flow rate, the maximum duration over time, and the minimum flow rate, computing an amplitude and a duration over time of an upstream variation as a function of the flow rate or the parameter correlated to the flow rate, the duration over time calculated using the duration over time interpolating curve, causing the upstream variation, by implementing the computed amplitude and the duration over time, of a value of the characteristic in the fresh treatment liquid with respect to said at least one prescription baseline, thereby causing a corresponding and timely delayed downstream variation of the same characteristic in the spent liquid flowing in the spent dialysate line, and computing at least one value of a parameter, indicative of the effectiveness of the extracorporeal treatment of blood, by using values correlated to the upstream variation of the value of the characteristic in the fresh treatment liquid and values correlated to the downstream variation of the same characteristic in the spent liquid.

2. An apparatus for an extracorporeal treatment of blood comprising:

a blood treatment unit having a primary chamber and a secondary chamber separated by a semi-permeable membrane;

a preparation line having one end connected to an inlet of the secondary chamber of the blood treatment unit and configured to convey fresh treatment liquid to the secondary chamber, the fresh treatment liquid presenting a characteristic selected from a group consisting of:

a conductivity in the fresh treatment liquid, and a concentration of at least one substance in the fresh treatment liquid;

a spent dialysate line having one end connected to an outlet of said secondary chamber and configured to remove spent liquid from the secondary chamber, the spent liquid presenting a characteristic selected from a group consisting of:

a conductivity in the spent liquid, and a concentration of at least one substance in the spent liquid; and a control unit configured to command execution of a task for determining a parameter indicative of an effectiveness of the extracorporeal treatment of blood, said task comprising the following steps:

receiving at least one prescription baseline for the characteristic in the fresh treatment liquid, receiving a flow rate, or a parameter correlated to the flow rate, of the fresh treatment liquid in the preparation line, causing the fresh treatment liquid to flow in the preparation line to the secondary chamber with the characteristic being at said at least one prescription baseline, causing the spent liquid to flow out of the secondary chamber into the spent dialysate line, computing an amplitude and a duration over time of an upstream variation as a function of the flow rate or the parameter correlated to the flow rate, causing the upstream variation, by implementing the computed amplitude and the duration over time, of a value of the characteristic in the fresh treatment liquid with respect to said at least one prescription baseline, thereby causing a corresponding and timely delayed downstream variation of the same characteristic in the spent liquid flowing in the spent dialysate line, and computing at least one value of a parameter indicative of the effectiveness of the extracorporeal treatment of blood by using values correlated to the upstream variation of the value of the characteristic in the fresh treatment liquid and values correlated to the downstream variation of the same characteristic in the spent liquid, wherein computing either or both the amplitude and the duration over time comprises selecting either or both the amplitude and the duration over time among a plurality of fixed amplitudes and/or fixed durations over time stored in the control unit and each corresponding to a range which the received flow rate falls in, wherein said range is one of a plurality of ranges of flow rates stored in the control unit.

3. An apparatus for an extracorporeal treatment of blood comprising:

a blood treatment unit having a primary chamber and a secondary chamber separated by a semi-permeable membrane;

a preparation line having one end connected to an inlet of the secondary chamber of the blood treatment unit and configured to convey fresh treatment liquid to the secondary chamber, the fresh treatment liquid presenting a characteristic selected from a group consisting of:

a conductivity in the fresh treatment liquid, and a concentration of at least one substance in the fresh treatment liquid;

a spent dialysate line having one end connected to an outlet of said secondary chamber and configured to remove spent liquid from the secondary chamber, the spent liquid presenting a characteristic selected from a group consisting of:

a conductivity in the spent liquid, and a concentration of at least one substance in the spent liquid; and a control unit configured to command execution of a task for determining a parameter indicative of an effectiveness of the extracorporeal treatment of blood, said task comprising the following steps:

receiving at least one prescription baseline for the characteristic in the fresh treatment liquid, receiving a flow rate, or a parameter correlated to the flow rate, of the fresh treatment liquid in the preparation line, causing the fresh treatment liquid to flow in the preparation line to the secondary chamber with the characteristic being at said at least one prescription baseline, causing the spent liquid to flow out of the secondary chamber into the spent dialysate line, computing an amplitude and a duration over time of an upstream variation as a function of the flow rate or the parameter correlated to the flow rate, causing the upstream variation, by implementing the computed amplitude and the duration over time, of a value of the characteristic in the fresh treatment liquid with respect to said at least one prescription baseline, thereby causing a corresponding and timely delayed downstream variation of the same characteristic in the spent liquid flowing in the spent dialysate line, and computing at least one value of a parameter, indicative of the effectiveness of the extracorporeal treatment of blood, by using values correlated to the upstream variation of the value of the characteristic in the fresh treatment liquid and values correlated to the downstream variation of the same characteristic in the spent liquid, wherein the task comprises causing the upstream variation of the value of the characteristic such that the upstream variation of the value of the characteristic is all above or all below the at least one prescription baseline, and wherein said amplitude is a difference between the at least one prescription baseline and a maximum or a minimum of the upstream variation.

4. The apparatus according to claim 1, wherein either or both the amplitude and the duration over time are higher if the flow rate is lower, and wherein either or both the amplitude and the duration over time are lower if the flow rate of the fresh treatment liquid is higher.

5. The apparatus according to claim 1, wherein computing either or both the amplitude and the duration over time is performed through at least one mathematical formula.

6. The apparatus according to claim 1, wherein computing the amplitude and the duration over time is performed through an interpolating curve, wherein the interpolating curve is computed starting from "m" points, each point being defined by a flow rate value of the fresh treatment liquid and by a duration over time corresponding to said flow rate value and/or by an amplitude corresponding to said flow rate value, wherein "m" is equal to or greater than two.

7. The apparatus according to claim 1, wherein the task further comprises:

receiving at least one mid duration over time corresponding to a mid flow rate of the apparatus, wherein the mid flow rate is between the maximum flow rate and the minimum flow rate; and computing the duration over time interpolating curve further based on the at least one mid duration over time and the mid flow rate.

8. The apparatus according to claim 3, wherein the duration over time is computed using a mathematical formula:

$$\Delta T=((\Delta T_{min}-\Delta T_{max})/(Q\text{dial}_{max}-Q\text{dial}_{min}))*(Q\text{dial}-Q\text{dial}_{max})+\Delta T_{min}$$

wherein:

Qdial is the flow rate of the fresh treatment liquid in the preparation line, $\text{Qdial}_{max}$ is a maximum flow rate of the apparatus, $\Delta T_{min}$ is a minimum duration over time corresponding to the maximum flow rate of the apparatus, $\text{Qdial}_{min}$ is a minimum flow rate of the apparatus, and $\Delta T_{max}$ is a maximum duration over time corresponding to the minimum flow rate of the apparatus.

9. The apparatus according to claim 1, wherein the task comprises:

receiving a minimum amplitude corresponding to a maximum flow rate of the apparatus;

receiving a maximum amplitude corresponding to a minimum flow rate of the apparatus;

computing an amplitude interpolating curve based on the minimum amplitude, the maximum flow rate, the maximum amplitude, and the minimum flow rate; and computing the amplitude through said amplitude interpolating curve.

10. The apparatus according to claim 9, wherein the task further comprises:

receiving at least one mid amplitude corresponding to a mid flow rate of the apparatus, wherein the mid flow rate is between the maximum flow rate and the minimum flow rate; and computing the amplitude interpolating curve further based on the at least one mid amplitude and the mid flow rate.

11. The apparatus according to claim 5, wherein the amplitude is computed using a mathematical formula:

$$\Delta C_{in}=((\Delta C_{min}-\Delta C_{max})/(Q\text{dial}_{max}-Q\text{dial}_{min}))*(Q\text{dial}-Q\text{dial}_{max})+\Delta C_{min}$$

wherein:

Qdial is the flow rate of the fresh treatment liquid in the preparation line, $\text{Qdial}_{max}$ is a maximum flow rate of the apparatus, $\Delta C_{min}$ is a minimum amplitude corresponding to the maximum flow rate, $\text{Qdial}_{min}$ is a minimum flow rate of the apparatus, and $\Delta C_{max}$ is a maximum amplitude corresponding to the minimum flow rate.

12. The apparatus according to claim 1, wherein computing either or both the amplitude and the duration over time comprises selecting either or both the amplitude and the duration over time among a plurality of fixed amplitudes and/or fixed durations over time stored in the control unit and each corresponding to a range which the received flow rate falls in, wherein said range is one of a plurality of ranges of flow rates stored in the control unit.

13. The apparatus according to claim 2, wherein said task comprises:

receiving "n" fixed durations over time; and receiving "n" ranges of the flow rate of the fresh treatment liquid, each of the "n" ranges being allocated to a fixed duration over time, wherein computing the duration over time comprises:

comparing the received flow rate with the "n" ranges, and selecting the fixed duration over time corresponding to a range of said "n" ranges which the flow rate falls in.

14. The apparatus according to claim 13, wherein the "n" fixed durations over time comprise:

a first duration over time, a second duration over time, and a third duration over time;

and wherein the "n" ranges of the flow rate comprise:

a first range, a second range, and a third range.

15. The apparatus according to claim 14, wherein:

the first duration over time is 150 seconds, the second duration over time is 120 seconds, the third duration over time is 90 seconds, the first range is between 300 and 400 ml/min, the second range is between 400 and 600 ml/min, and the third range is between 600 and 800 ml/min.

16. The apparatus according to claim 2, wherein said task comprises:

receiving "n" fixed amplitudes; and receiving "n" ranges of the flow rate of the fresh treatment liquid, each of the "n" ranges being allocated to a fixed amplitude, wherein computing the amplitude comprises:

comparing the received flow rate with the "n" ranges, and selecting the fixed amplitude corresponding to a range of said "n" ranges which the flow rate falls in.

17. The apparatus according to claim 1, wherein said task comprises causing the upstream variation of the value of the characteristic such that the upstream variation of the value of the characteristic is all above or all below the at least one prescription baseline, and wherein said amplitude is a difference between the at least one prescription baseline and a maximum or a minimum of the upstream variation.

18. The apparatus according to claim 1, wherein said task comprises causing the upstream variation of the value of the characteristic such that the upstream variation of the value of the characteristic comprises at least one part above the at least one prescription baseline and at least one part below the at least one prescription baseline, and wherein said amplitude is a difference between a maximum and a minimum of the upstream variation.

19. The apparatus according to claim 18, wherein said task comprises causing the upstream variation of the value of the characteristic such that the upstream variation of the value of the characteristic has a rectangular shape or is bell-shaped.

20. The apparatus according to claim 18, wherein said task comprises causing the upstream variation of the value of the characteristic such that a total area of parts of the upstream variation of the value of the characteristic above the at least one prescription baseline is equal to a total area of the parts of the upstream variation of the value of the characteristic below the at least one prescription baseline.

21. The apparatus according to claim 18, wherein said task comprises:

receiving a maximum allowed value of the characteristic in the fresh treatment liquid;

receiving a minimum allowed value of the characteristic in the fresh treatment liquid; and causing the upstream variation of the value of the characteristic such that said upstream variation is all between the minimum allowed value of the characteristic and the maximum allowed value of the characteristic.

22. The apparatus according to claim 1, wherein receiving a flow rate, or a parameter correlated to the flow rate, of the fresh treatment liquid in the preparation line comprises:

in a hemodialysis treatment, receiving an effluent flow rate and an ultrafiltration flow rate and calculating the flow rate, or the parameter correlated to the flow rate, based on the effluent flow rate and on the ultrafiltration flow rate; and in a hemodiafiltration treatment, receiving an effluent flow rate, an infusion flow rate and an ultrafiltration flow rate and calculating the flow rate, or the parameter correlated to the flow rate, based on the effluent flow rate, the infusion flow rate and on the ultrafiltration flow rate.

23. The apparatus according to claim 1, wherein the control unit executes the task including:

receiving a blood or plasma flow rate at the inlet of the primary chamber; and computing either or both said amplitude and said duration over time of the upstream variation to be caused also as a function of the blood or plasma flow rate.

24. The apparatus according to claim 1, wherein the control unit executes the task including:

receiving an efficiency parameter of the blood treatment unit, wherein the efficiency parameter is selected between a clearance or a dialysance or a mass transfer area coefficient, and computing either or both said amplitude and said duration over time of the upstream variation to be caused also as a function of the efficiency parameter of the blood treatment unit.

25. The apparatus according to claim 1, wherein the computed duration over time is comprised between a prefixed minimum duration over time of 50 seconds, and a prefixed maximum duration over time of 200 seconds, and the characteristic is the conductivity in the fresh treatment liquid and the computed amplitude of conductivity is between 0.4 mS/cm and 1.1 mS/cm as absolute values.

* * * * *